US 12,121,587 B1

(12) United States Patent
Lim

(10) Patent No.: US 12,121,587 B1
(45) Date of Patent: *Oct. 22, 2024

(54) DIMERIC ANTIBODIES

(71) Applicant: Medicovestor, Inc., Wilmington, DE (US)

(72) Inventor: Seah Lim, Wilmington, DE (US)

(73) Assignee: MEDICOVESTOR, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/396,418

(22) Filed: Dec. 26, 2023

(51) Int. Cl.
*C07K 16/46* (2006.01)
*A61K 47/68* (2017.01)

(52) U.S. Cl.
CPC .......... *A61K 47/6811* (2017.08); *C07K 16/46* (2013.01)

(58) Field of Classification Search
None
See application file for complete search history.

(56) References Cited

U.S. PATENT DOCUMENTS

| | | | |
|---|---|---|---|
| 5,731,168 A | 3/1998 | Carter et al. | |
| 6,897,044 B1 * | 5/2005 | Braslawsky | A61P 1/00 435/69.6 |
| 8,592,562 B2 | 11/2013 | Kannan et al. | |
| 9,505,848 B2 | 11/2016 | Davis et al. | |
| 9,862,769 B2 | 1/2018 | De Goeij et al. | |
| 10,011,858 B2 | 7/2018 | Igawa et al. | |
| 10,344,050 B2 | 7/2019 | Gramer et al. | |
| 10,597,464 B2 | 3/2020 | Labrijn et al. | |
| 2015/0038682 A1 * | 2/2015 | Tsurushita | C07K 16/2878 530/387.3 |

OTHER PUBLICATIONS

Caron et al., J. Exp. Med. 176:1191-95 (Year: 1992).*
Almagro & Fransson, Frontiers in Bioscience 13:1619-33 (Year: 2008).*
Shopes, B., "A genetically engineered human IgG mutant with enhanced cytolytic activity," The Journal of Immunology, May 1, 1992;148(9):2918-22.
Shopes, B., "A genetically engineered human IgG with limited flexibility fully initiates cytolysis via complement," Molecular Immunology, Apr. 1993;30(6):603-9.
Van der Neut Kolfschoten, M. et al., "Anti-inflammatory activity of human IgG4 antibodies by dynamic Fab arm exchange," Science, Sep. 14, 2007;317(5844):1554-7.

* cited by examiner

*Primary Examiner* — Jessica H Roark
(74) *Attorney, Agent, or Firm* — HOLLAND & HART LLP

(57) ABSTRACT

This disclosure relates to dimeric immunotherapeutics that comprise two IgGs that are crosslinked with a disulfide bond. The two IgGs may be chimeras of two different heavy chains, in which one heavy chain includes a cysteine mutation that forms the disulfide bond, and the other heavy chain lacks the cysteine mutation. The presence of a cysteine mutation in only one of the heavy chains of an IgG avoids two disulfide bonds between the two IgGs, which increases the accessible orientations between the two crosslinked IgGs, and also avoids the formation of trimers and higher-order oligomers.

20 Claims, 4 Drawing Sheets

Specification includes a Sequence Listing.

DIMERIC ANTIBODIES

TECHNICAL FIELD

The present disclosure relates to antibodies that are cross-linked with a disulfide bond to form dimers as well as methods to manufacture such dimers.

SEQUENCE LISTING

This disclosure includes a sequence listing, which has file name "sequence_listing_1200590009.xml," which was created on Dec. 26, 2023, and which has a file size of 10,451 bytes, and which is incorporated by reference in its entirety.

BACKGROUND OF SOME ASPECTS OF THIS SPECIFICATION

Therapeutic antibodies are responsible for tremendous improvements in cancer outcomes and present new opportunities to cure cancer, at least in a subset of patients. The first antibody cancer immunotherapeutic Rituxan® was approved to treat B-cell non-Hodgkin's lymphoma in the United States in 1997 and has over $100 billion in lifetime sales. Rituxan® still sells over $1 billion annually despite extensive competition. The competing antibody Zevalin®, for example, was approved in the United States in 2002. Both Rituxan® and Zevalin® target CD20, which is a B-cell antigen, and both immunotherapeutics act by depleting B cells. When Rituxan® binds CD20, it triggers antibody-dependent cellular toxicity and leukocyte-mediated cell death, whereas Zevalin® is chemically modified to chelate a radioisotope, which additionally allows for radiation-induced cell death. Therapeutic antibodies may also be conjugated to cytotoxic pharmaceuticals with labile linkers that allow for antibody-drug conjugates that release their cytotoxic payloads upon binding an antigen. Numerous other antibody-based strategies exist as cancer treatments.

Toward the end of the twentieth century, dimeric antibodies were assessed as possible immunotherapeutics. Dimeric antibodies may be produced by chemical crosslinking or with engineered disulfide bonds. Chemical crosslinking generally modifies lysine amino acids, which are prevalent in antibodies, and thus, chemical crosslinking creates a heterogenous population of different dimers that display varying pharmacological effects. Engineered disulfide bonds reduce heterogeneity, but no chemically-crosslinked dimer nor any disulfide linked dimer has ever received marketing approval to treat health conditions in humans.

While therapeutic antibodies revolutionized the field of medicine, progress remains incremental. Innovative strategies that improve upon existing antibody technologies remain desirable.

SUMMARY OF SOME ASPECTS OF THE SPECIFICATION

Various aspects of this disclosure relate to the development of improved methods to manufacture disulfide-linked dimeric antibodies. Briefly, a cysteine mutation is introduced into a first IgG antibody. As shown in FIG. 1, the first IgG antibody is then combined with a second IgG antibody under mild reducing conditions to reduce disulfide bonds that crosslink the two different heavy chains of the IgGs. The IgGs then separate and reform as chimeric antibodies, which comprise a heavy chain and a light chain from each of the first IgG and the second IgG. The chimeric antibodies are then subjected to mild oxidizing conditions to form disulfide-linked dimers of the chimeric antibodies. The disulfide-linked dimers of this specification are identified as "dimeric immunotherapeutics."

This disclosure uses the term "chimeric antibody" differently than as commonly used in the field of immunology. In this disclosure, the term "chimeric antibody" refers to an IgG antibody that has one or both of (1) two heavy chains that comprise two different amino acid sequences and (2) two light chains that comprise two different amino acid sequences. Methods of producing such chimeric antibodies are described, for example, in U.S. Pat. Nos. 9,862,769 B2 and 10,344,050 B2, which are incorporated by reference in their entireties. These methods, which are branded as the DuoBody® platform (Genmab, Denmark), were developed to manufacture bispecific antibodies that bind two different antigens. While the chimeric antibodies of this disclosure may optionally bind two different antigens, the novelty and advantages of this disclosure arise from a cysteine mutation that is present on only a single chain of a chimeric antibody, which allows for the chimeric antibody to form a single disulfide bond.

The heavy chains or light chains of a chimeric antibody have two different amino acid sequences at least because either one of the heavy chains or one of the light chains includes a cysteine mutation to allow for the single disulfide bond. U.S. Pat. Nos. 9,862,769 B2 and 10,344,050 B2 also describe additional mutations that favor separation of the heavy chains of an IgG such as F405L and K409R mutations to IgG1s. Such additional mutations, however, are not required to engineer chimeric antibodies. The additional mutations instead simply increase relative yields. The amino acid sequences may also vary, for example, either to manufacture dimers of bispecific antibodies, as an artifact from cloning, or for other reasons that do not limit this disclosure.

The inventor discovered a defect in historical disulfide-linked dimeric antibodies that the dimeric immunotherapeutics of this disclosure remedy. Antibodies contain multiple copies of the same amino acid sequences, and thus, engineering a cysteine into an antibody results in more cysteines than necessary to form a disulfide bond. IgGs, for example, contain two copies of each amino acid sequence. The additional cysteines remain available for mischief such as by forming additional intramolecular disulfide bonds, which risk constraining the accessible conformations of a dimer, or by crosslinking the dimer to either additional antibodies or entirely different molecules. The dimeric immunotherapeutics of this disclosure comprise two antibodies engineered to contain only a single cysteine each, and thus, they overcome this previously-unappreciated historical problem by eliminating the deleterious additional cysteines.

This disclosure focuses on IgG1 antibodies, but the innovation of this disclosure is generally compatible with any IgG antibody. IgG4 antibodies, for example, readily chimerize in the presence of 2-mercaptoethanol, molecular cysteine, and glutathione as described, for example, in van der Neut Kolfschoten, M. et al., "Anti-inflammatory activity of human IgG4 antibodies by dynamic Fab arm exchange," SCIENCE, 2007 Sep. 14; 317(5844): 1554-57.

The preceding Background and Summary sections are provided as a brief introduction to the described subject matter as well as a synopsis of some of the technological improvements and advantages that it provides. The Background and Summary shall not be construed as identifying essential aspects of the described subject matter, nor shall they be construed to limit the interpretation of this specification or any patent claim that matures from this specification.

BRIEF DESCRIPTION OF THE DRAWINGS

A further understanding of this specification may be appreciated with reference to the following drawings. The drawings are exemplary, and neither this specification nor any patent claim that matures from this specification shall be construed as limited by the drawings.

DETAILED DESCRIPTION

Figure 1:
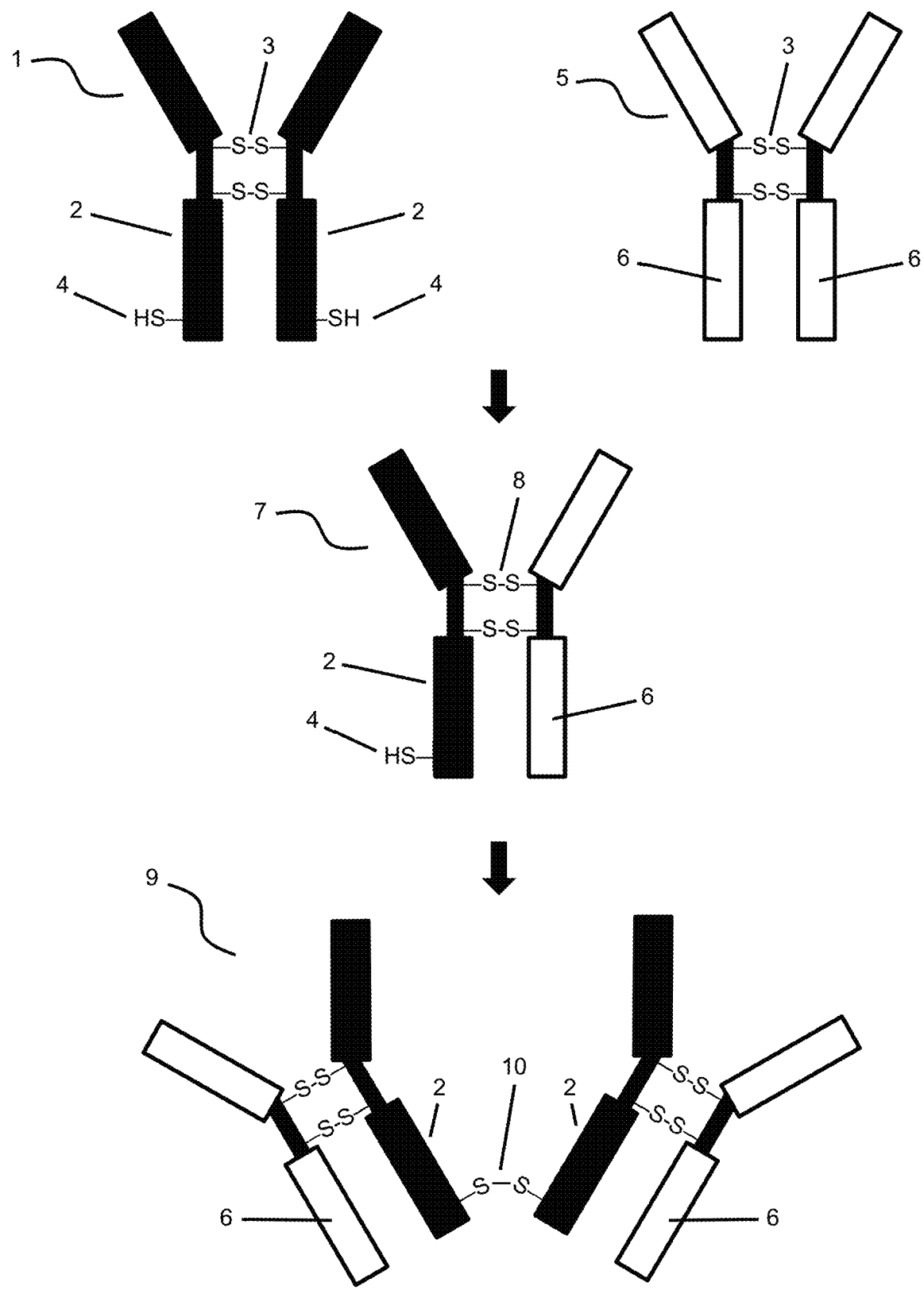
FIG. 1 is a cartoon that depicts a general method to produce dimeric immunotherapeutics, in which a single disulfide bond crosslinks two different IgGs.

Various aspects of this disclosure relate to a method to manufacture a dimeric immunotherapeutic. FIG. 1 is a drawing that depicts a method of this disclosure. A first IgG 1 is provided, which comprises two half molecules 2 that each comprise a heavy chain and a light chain. The amino acid sequence of the heavy chain is the same for each half molecule 2, and the amino acid sequence of the light chain is the same for each half molecule 2. The two half molecules 2 are crosslinked with disulfide bonds 3, which occur at the hinge regions of the first IgG 1. Each half molecule 2 comprises a mutation of a native amino acid to cysteine 4, which may occur in either the heavy chains or the light chains. The first IgG 1 comprises two such cysteine mutations 4, which are depicted as present on the heavy chains.

A second IgG 5 is also provided, which comprises two half molecules 6 that each comprise a heavy chain and a light chain. The amino acid sequence of the heavy chain is the same for each half molecule 6, and the amino acid sequence of the light chain is the same for each half molecule 6. The two half molecules 6 are crosslinked with disulfide bonds 3, which occur at the hinge regions of the second IgG 5. Each half molecule 6 lacks the mutation of the native amino acid to cysteine.

The first IgG 1 and the second IgG 5 are combined under mild reducing conditions, such as in the presence of cysteamine, to reduce the disulfide bonds 3 without reducing other disulfide bonds of the first IgG 1 and the second IgG 5. Other disulfide bonds include disulfide bonds that covalently attach the light chains to the heavy chains and disulfide bonds that enforce tertiary structure. Non-limiting examples of suitable reducing agents include cysteamine.

Following reduction of the disulfide bonds 3, the half molecules 2 of the first IgG 1 may dissociate, the half molecules 6 of the second IgG 5 may dissociate, and a half molecule 2 of the first IgG 1 may then pair with a half molecule 6 of the second IgG 5. Various mutations such as F405L and K409R (as described herein when the first IgG 1 and the second IgG 5 are IgG1s) may favor one or both of dissociation of two half molecules 2, 6 of the first IgG 1 and/or the second IgG 5 and the pairing of a half molecule 2 of the first IgG 1 with a half molecule 6 of the second IgG 5.

After incubating the first IgG 1 and the second IgG 5 under reducing conditions that allow for the two half molecules 2, 6 of the first IgG 1 and the second IgG 5 to dissociate and then pair, the paired half molecules 2,6 of the first IgG 1 and the second IgG 5 are oxidized to form disulfide bonds 8 that crosslink the half molecule 2 of the first IgG 1 to the half molecule 6 of the second IgG 5 and result in a chimeric immunotherapeutic 7. The chimeric immunotherapeutic 7 contains a single half molecule 2 of the first IgG 1 such that the chimeric immunotherapeutic 7 comprises a single mutation of a native amino acid to cysteine 4.

After incubating the first IgG 1 and the second IgG 5 under reducing conditions that allow for the two half molecules 2, 6 of the first IgG 1 and the second IgG 5 to dissociate and then pair, the cysteines 4 of two different chimeric immunotherapeutics 7 are oxidized to form a disulfide bond 10 that crosslinks the two different chimeric immunotherapeutics 7 to form a dimeric immunotherapeutic 9.

FIG. 1 depicts the disulfide bonds 8 of the chimeric immunotherapeutic 7 forming prior to the disulfide bond 10 that crosslinks the two different chimeric immunotherapeutics 7 to form the dimeric immunotherapeutic 9, and these disulfide bonds 8 likely form prior to the disulfide bond 10 that crosslinks the two different chimeric immunotherapeutics 7, for example, due to proximity enforced by noncovalent interactions between the half molecules 2, 6 of the first IgG 1 and the second IgG 5. The order depicted in FIG. 1 nevertheless shall not limit this disclosure or any patent claim that matures from this disclosure, for example, as the disulfide bond 10 that crosslinks the two different chimeric immunotherapeutics 7 may form either contemporaneously with the disulfide bonds 8 that crosslink the half molecules 2,6 of the first IgG 1 and the second IgG 5 or even prior to formation of these disulfide bonds 8.

In some embodiments, the method comprises providing a first immunotherapeutic and a second immunotherapeutic. In some specific embodiments, the first immunotherapeutic comprises a first IgG, and the second immunotherapeutic comprises a second IgG. In some very specific embodiments, the first immunotherapeutic is the first IgG, and the second immunotherapeutic is the second IgG. The first immunotherapeutic may nevertheless comprise the first IgG and a covalently attached linker for conjugation of a pharmaceutical payload or a chelator of the first immunotherapeutic to the first IgG; and/or the second immunotherapeutic may comprise the second IgG and a covalently attached linker for conjugate of a same or different pharmaceutical payload or a same or different chelator of the second immunotherapeutic to the second IgG.

The nature of the first IgG and the second IgG is not limiting. The first IgG may be selected from an IgG1, IgG2, IgG3, and IgG4, for example, and the second IgG may be selected from an IgG1, IgG2, IgG3, and IgG4. In some embodiments, both the first IgG and the second IgG are each either an IgG1, IgG2, IgG3, or IgG4 such that the first IgG and the second IgG are the same type of IgG.

The first IgG may be selected from a chimeric human/animal antibody (such as a chimeric human/mouse antibody), a humanized antibody, and a fully-human antibody, and the second IgG may be selected from a chimeric human/animal antibody (such as a chimeric human/mouse antibody), a humanized antibody, and a fully-human antibody. In some embodiments, both the first IgG and the second IgG are each either a chimeric human/animal antibody, a humanized antibody, and a fully-human antibody such that the first IgG and the second IgG are the same type of IgG.

The term "chimeric human/animal antibody" uses the term "chimeric" as conventionally used in relation to the term "antibody," and thus, the term "chimeric human/animal antibody" is different from the term "chimeric antibody" as the terms are used in this disclosure.

In some embodiments, the first IgG comprises a human heavy chain constant domain 3 (CH3 region). In some embodiments, the second IgG comprises a human CH3 region. In some specific embodiments, the first IgG and the second IgG comprise human CH3 regions.

The first IgG is typically a monoclonal antibody. In some embodiments, both the first IgG and the second IgG are monoclonal antibodies.

In some embodiments, the first IgG has at least 95 percent amino acid sequence identity with a therapeutic antibody selected from 3F8, abagovomab, abituzumab, adecatumumab, amatuximab, andecaliximab, anrukinzumab, apolizumab, ascrinvacumab, atezolizumab, avelumab, basiliximab, bavituximab, belimumab, bemarituzumab, bermekimab, bevacizumab, bivatuzumab, bleselumab, blontuvetmab, brontictuzumab, cabiralizumab, camrelizumab, capromab, carotuximab, cemiplimab, cetrelimab, cetuximab, cibisatamab, cirmtuzumab, cixutumumab, clazakizumab, codrituzumab, conatumumab, cusatuzumab, dacetuzumab, daclizumab, dalotuzumab, daratumumab, dectrekumab, demcizumab, detumomab, dinutuximab, dinutuximab beta, dostarlimab, drozitumab, duligotuzumab, durvalumab, dusigitumab, ecromeximab, edrecolomab, eldelumab, elgemtumab, elotuzumab, elsilimomab, emactuzumab, emibetuzumab, enavatuzumab, enoblituzumab, enoticumab, ensituximab, epratuzumab, etaracizumab, etigilimab, faricimab, farletuzumab, fibatuzumab, ficlatuzumab, figitumumab, flanvotumab, fresolimumab, futuximab, galiximab, ganitumab, gatipotuzumab, gevokizumab, gilvetmab, gimsilumab, girentuximab, gomiliximab, icrucumab, ifabotuzumab, imalumab, imaprelimab, imgatuzumab, inebilizumab, inolimomab, intetumumab, ipilimumab, iratumumab, isatuximab, iscalimab, istiratumab, labetuzumab, lacnotuzumab, lebrikizumab, lenzilumab, leronlimab, lexatumumab, lintuzumab, lirilumab, lucatumumab, lulizumab pegol, lumiliximab, lumretuzumab, lutikizumab, mapatumumab, margetuximab, matuzumab, milatuzumab, mitumomab, modotuximab, mogamulizumab, monalizumab, namilumab, narnatumab, navicixizumab, naxitamab, necitumumab, nesvacumab, nimotuzumab, nivolumab, obinutuzumab, ocaratuzumab, ocrelizumab, ofatumumab, olaratumab, oleclumab, olokizumab, omburtamab, ontuxizumab, oregovomab, otlertuzumab, panitumumab, pankomab, parsatuzumab, pasotuxizumab, patritumab, pembrolizumab, pemtumomab, pertuzumab, pidilizumab, pritumumab, prolgolimab, racotumomab, radretumab, ramucirumab, ravagalimab, relatlimab, retifanlimab, rilotumumab, rinucumab, rituximab, robatumumab, romilkimab, rosmantuzumab, samalizumab, sarilumab, selicrelumab, seribantumab, sibrotuzumab, siltuximab, sintilimab, sirukumab, spartalizumab, tabalumab, tafasitamab, talacotuzumab, tarextumab, tavolimab, telisotuzumab, tenatumomab, teneliximab, tepoditamab, teprotumumab, theralizumab, tigatuzumab, timigutuzumab, tiragotumab, tislelizumab, tomuzotuximab, tositumomab, tovetumab, tralokinumab, trastuzumab, tremelimumab, ublituximab, ulocuplumab, urelumab, utomilumab, vanalimab, vantictumab, vanucizumab, varisacumab, varlilumab, veltuzumab, volociximab, vonlerolizumab, votumumab, xentuzumab, zalutumumab, zatuximab, zenocutuzumab, and zolbetuximab. In some specific embodiments, the first IgG has at least 98 percent amino acid sequence identity with the therapeutic antibody. In some very specific embodiments, the first IgG has at least 99 percent amino acid sequence identity with the therapeutic antibody. The first IgG lacks 100 percent amino acid sequence identity with the therapeutic antibody because the first IgG comprises a mutation of a native amino acid to a cysteine (such as either S444C or S119C) to allow for a disulfide bond that crosslinks chimeric IgGs of a dimeric immunotherapeutic. The first IgG may also lack 100 percent amino acid sequence identity with the therapeutic antibody, for example, to introduce one or more mutations that favor dissociation of half molecules of the first IgG (such as either F405L or K409R). The first IgG may also lack 100 percent amino acid sequence identity with the therapeutic antibody, for example, to remove or alter glycosylation sites, to modulate effector function, to modulate half-life in vivo, to improve stability, to reduce antigenicity in vivo, as an artifact of cloning, and/or for any number of other reasons.

In some embodiments, the first IgG has at least 95 percent amino acid sequence with a therapeutic antibody set forth in the preceding paragraph, and the second IgG has at least 95 percent amino acid sequence identity with the same therapeutic antibody. In some specific embodiments, the first IgG has at least 98 percent amino acid sequence with a therapeutic antibody set forth in the preceding paragraph, and the second IgG has at least 98 percent amino acid sequence identity with the same therapeutic antibody. In some very specific embodiments, the first IgG has at least 99 percent amino acid sequence with a therapeutic antibody set forth in the preceding paragraph, and the second IgG has at least 99 percent amino acid sequence identity with the same therapeutic antibody.

In some embodiments, the first IgG has at least 95 percent amino acid sequence with the therapeutic antibody; the first IgG specifically binds an antigen; and the second IgG is a different therapeutic antibody that binds a different epitope of the same antigen. In some specific embodiments, the first IgG has at least 98 percent amino acid sequence with the therapeutic antibody. In some very specific embodiments, the first IgG has at least 99 percent amino acid sequence with the therapeutic antibody.

In some embodiments, the first IgG has at least 95 percent amino acid sequence with the therapeutic antibody; the first IgG specifically binds an antigen; and the second IgG is a different therapeutic antibody that binds a different antigen. In some specific embodiments, the first IgG has at least 98 percent amino acid sequence with the therapeutic antibody. In some very specific embodiments, the first IgG has at least 99 percent amino acid sequence with the therapeutic antibody.

In some embodiments, the first immunotherapeutic is a variant of a parent immunotherapeutic selected from 3F8, abagovomab, abituzumab, adecatumumab, amatuximab, andecaliximab, anrukinzumab, apolizumab, ascrinvacumab, atezolizumab, avelumab, basiliximab, bavituximab, belimumab, bemarituzumab, bermekimab, bevacizumab, bivatuzumab, bleselumab, blontuvetmab, brontictuzumab, cabiralizumab, camrelizumab, capromab, carotuximab, cemiplimab, cetrelimab, cetuximab, cibisatamab, cirmtuzumab, cixutumumab, clazakizumab, codrituzumab, conatumumab, cusatuzumab, dacetuzumab, daclizumab, dalotuzumab, daratumumab, dectrekumab, demcizumab, detumomab, dinutuximab, dinutuximab beta, dostarlimab, drozitumab, duligotuzumab, durvalumab, dusigitumab, ecromeximab, edrecolomab, eldelumab, elgemtumab, elotuzumab, elsilimomab, emactuzumab, emibetuzumab, enavatuzumab, enoblituzumab, enoticumab, ensituximab, epratuzumab, etaracizumab, etigilimab, faricimab, farletuzumab, fibatuzumab, ficlatuzumab, figitumumab, flanvotumab, fresolimumab, futuximab, galiximab, ganitumab, gatipotuzumab, gevokizumab, gilvetmab, gimsilumab, girentuximab, gomiliximab, icrucumab, ifabotuzumab, imalumab, imaprelimab, imgatuzumab, inebilizumab, inolimomab, intetumumab, ipilimumab, iratumumab, isatuximab, iscalimab, istiratumab, labetuzumab, lacnotuzumab, lebrikizumab, lenzilumab, leronlimab, lexatumumab, lintuzumab, lirilumab, lucatumumab, lulizumab pegol, lumiliximab, lumretuzumab, lutikizumab, mapatumumab, margetuximab, matuzumab, milatuzumab, mitumomab, modotuximab, mogamulizumab, monalizumab, namilumab, narnatumab, navicixizumab, naxitamab, necitumumab, nesvacumab, nimotuzumab, nivolumab, obinutuzumab, ocaratuzumab, ocrelizumab, ofatumumab, olaratumab, oleclumab, olokizumab, omburtamab, ontuxizumab, oregovomab, otlertuzumab, panitumumab, pankomab, parsatuzumab, pasotuxizumab, patritumab, pembrolizumab, pemtumomab, pertuzumab, pidilizumab, pritumumab, prolgolimab, racotumomab, radretumab, ramucirumab, ravagalimab, relatlimab, retifanlimab, rilotumumab, rinucumab, rituximab, robatumumab, romilkimab, rosmantuzumab, samalizumab, sarilumab, selicrelumab, seribantumab, sibrotuzumab, siltuximab, sintilimab, sirukumab, spartalizumab, tabalumab, tafasitamab, talacotuzumab, tarextumab, tavolimab, telisotuzumab, tenatumomab, teneliximab, tepoditamab, teprotumumab, theralizumab, tigatuzumab, timigutuzumab, tiragotumab, tislelizumab, tomuzotuximab, tositumomab, tovetumab, tralokinumab, trastuzumab, tremelimumab, ublituximab, ulocuplumab, urelumab, utomilumab, vanalimab, vanticumab, vanucizumab, varisacumab, varlilumab, veltuzumab, volociximab, vonlerolizumab, votumumab, xentuzumab, zalutumumab, zatuximab, zenocutuzumab, zolbetuximab, anetumab ravtansine, aprutumab ixadotin, azintuxizumab vedotin, belantamab mafodotin, brentuximab vedotin, camidanlumab tesirine, cantuzumab mertansine, cantuzumab ravtansine, cbr96-doxorubicin immunoconjugate, cergutuzumab amunaleukin, cofetuzumab pelidotin, coltuximab ravtansine, denintuzumab mafodotin, depatuxizumab mafodotin, derbyotuximab biotin, enapotamab vedotin, enfortumab vedotin, gemtuzumab ozogamicin, glembatumumab vedotin, iladatuzumab vedotin, indatuximab ravtansine, indusatumab vedotin, inotuzumab ozogamicin, ladiratuzumab vedotin, laprituximab emtansine, lifastuzumab vedotin, loncastuximab tesirine, lorvotuzumab mertansine, losatuxizumab vedotin, mirvetuximab soravtansine, moxetumomab pasudotox, naratuximab emtansine, pinatuzumab vedotin, polatuzumab vedotin, rovalpituzumab tesirine, sacituzumab govitecan, samrotamab vedotin, sirtratumab vedotin, sofituzumab vedotin, taplitumomab paptox, telisotuzumab vedotin, tisotumab vedotin, trastuzumab deruxtecan, trastuzumab duocarmazine, trastuzumab emtansine, tucotuzumab celmoleukin, vadastuximab talirine, vandortuzumab vedotin, vorsetuzumab mafodotin, clivatuzumab tetraxetan, ibritumomab tiuxetan, lilotomab satetraxetan, tacatuzumab tetraxetan, and tositumomab, wherein the first immunotherapeutic is a variant of the parent immunotherapeutic because the amino acid sequences of the first IgG of the first immunotherapeutic contain one or more mutations relative to the amino acid sequences of the parent immunotherapeutic, which one or more mutations comprise a mutation of a native amino acid to a cysteine (such as either S444C or S119C) and optionally comprise one or more additional mutations such as one or more mutations that favor dissociation of half molecules of the first IgG under reducing conditions (such as either F405L or K409R).

In some embodiments, the first immunotherapeutic is a variant of the parent immunotherapeutic; the second immunotherapeutic is either a second parent immunotherapeutic of the preceding paragraph or a variant of a second parent immunotherapeutic of the preceding paragraph; the first immunotherapeutic is a variant of the parent immunotherapeutic because the amino acid sequences of the first IgG of the first immunotherapeutic contain one or more mutations relative to the amino acid sequences of the parent immunotherapeutic, which one or more mutations comprise a mutation of a native amino acid to a cysteine (such as either S444C or S119C) and optionally comprise one or more additional mutations such as one or more mutations that favor dissociation of half molecules of the first IgG under reducing conditions (such as either F405L or K409R); and the second immunotherapeutic is optionally a variant of the second parent immunotherapeutic because the amino acid sequences of the second IgG of the second immunotherapeutic contain one or more mutations relative to the amino acid sequences of the second parent immunotherapeutic, such as one or more mutations that favor dissociation of half molecules of the second IgG under reducing conditions (such as either F405L or K409R). The parent immunotherapeutic and the second parent immunotherapeutic are optionally the same or different parent immunotherapeutics of the preceding paragraph. In some specific embodiments, the parent immunotherapeutic and the second parent immunotherapeutic are the same parent immunotherapeutic of the preceding paragraph.

When the parent immunotherapeutic is a radioimmunoconjugate such as clivatuzumab tetraxetan, ibritumomab tiuxetan, lilotomab satetraxetan, tacatuzumab tetraxetan, or tositumomab, then the first immunotherapeutic (or the second immunotherapeutic) may be a variant of the parent immunotherapeutic because, unlike the parent immunotherapeutic, the first immunotherapeutic (or the second immunotherapeutic) generally does not chelate a radioisotope until use of a dimeric immunotherapeutic, for example, in a method of imaging or treating cancer.

The first IgG comprises two heavy chains that have a first amino acid sequence, and the second IgG comprises two heavy chains that have a second amino acid sequence. The first immunotherapeutic comprises two heavy chains because the first IgG comprises two heavy chains, and the second immunotherapeutic comprises two heavy chains because the second IgG comprises two heavy chains. In other words, the two heavy chains of the first IgG and the first immunotherapeutic are the same heavy chains, and the two heavy chains of the second IgG and second first immunotherapeutic are the same heavy chains.

The first IgG comprises two light chains that have a first light chain amino acid sequence, and the second IgG comprises two light chains that have a second light chain amino acid sequence. The first immunotherapeutic comprises two light chains because the first IgG comprises two light chains, and the second immunotherapeutic comprises two light chains because the second IgG comprises two light chains. In other words, the two light chains of the first IgG and the first immunotherapeutic are the same light chains, and the two light chains of the second IgG and second first immunotherapeutic are the same light chains.

In some embodiments, the first amino acid sequence includes a mutation of a native amino acid to a cysteine, and the second amino acid sequence lacks the mutation. In some specific embodiments, the first amino acid sequence includes a mutation of a native amino acid to a cysteine; the second amino acid sequence lacks the mutation; the first light chain amino acid sequence lacks the mutation; and the second light chain amino acid sequence lacks the mutation. In other words, the first amino acid sequence of the heavy chain of the first IgG comprises the mutation.

This disclosure contemplates "a mutation of a native amino acid to a cysteine," which occurs on either a heavy chain or a light chain of the first IgG, and this disclosure is generally structured to disclose a feature in combination with the mutation of the native amino acid to a cysteine, which occurs on a heavy chain, followed by a paragraph that discloses a similar feature in combination with the mutation of the native amino acid to a cysteine, which occurs on the light chain, as applicable, to provide explicit support for both configurations.

In some embodiments, the first light chain amino acid sequence includes a mutation of a native amino acid to a cysteine, and the second light chain amino acid sequence lacks the mutation. In some specific embodiments, the first light chain amino acid sequence includes a mutation of a native amino acid to a cysteine; the second light chain amino acid sequence lacks the mutation; the first amino acid sequence lacks the mutation; and the second amino acid sequence lacks the mutation. In other words, the first light chain amino acid sequence of the light chain of the first IgG comprises the mutation.

In some embodiments, the two heavy chains of the first IgG and the two heavy chains of the second IgG are different heavy chains, and the two heavy chains of the first immunotherapeutic and the two heavy chains of the second immunotherapeutic are therefore also different heavy chains. In some specific embodiments, the two heavy chains of the first IgG and the two heavy chains of the second IgG are different heavy chains; the two heavy chains of the first immunotherapeutic and the two heavy chains of the second immunotherapeutic are therefore also different heavy chains; the two heavy chains of the first IgG comprise a mutation of a native amino acid to a cysteine; and the two heavy chains of the second IgG lack the mutation. In some very specific embodiments, the two heavy chains of the first IgG and the two heavy chains of the second IgG are different heavy chains; the two heavy chains of the first immunotherapeutic and the two heavy chains of the second immunotherapeutic are therefore also different heavy chains; the two heavy chains of the first IgG comprise a mutation of a native amino acid to a cysteine; the two heavy chains of the second IgG lack the mutation; the two light chains of the first IgG lack the mutation; and the two light chains of the second IgG lack the mutation. In some embodiments, the two light chains of the first IgG and the two light chains of the second IgG each have identical amino acid sequences (in contrast with the two heavy chains of the first IgG and the two heavy chains of the second IgG, which are different heavy chains).

In some embodiments, the two light chains of the first IgG and the two light chains of the second IgG are different light chains, and the two light chains of the first immunotherapeutic and the two light chains of the second immunotherapeutic are therefore also different light chains. In some specific embodiments, the two light chains of the first IgG and the two light chains of the second IgG are different light chains; the two light chains of the first immunotherapeutic and the two light chains of the second immunotherapeutic are therefore also different light chains; the two light chains of the first IgG comprise a mutation of a native amino acid to a cysteine; and the two light chains of the second IgG lack the mutation. In some very specific embodiments, the two light chains of the first IgG and the two light chains of the second IgG are different light chains; the two light chains of the first immunotherapeutic and the two light chains of the second immunotherapeutic are therefore also different light chains; the two light chains of the first IgG comprise a mutation of a native amino acid to a cysteine; the two light chains of the second IgG lack the mutation; the two heavy chains of the first IgG lack the mutation; and the two heavy chains of the second IgG lack the mutation. In some embodiments, the two heavy chains of the first immunotherapeutic and the two heavy chains of the second immunotherapeutic each have identical amino acid sequences (in contrast with the two light chains of the first IgG and the two light chains of the second IgG, which are different light chains).

In some embodiments, the two heavy chains of the first immunotherapeutic are covalently crosslinked with a first one or more disulfide bond(s), and the two heavy chains of the second immunotherapeutic are covalently crosslinked with a second one or more disulfide bond(s). In some specific embodiments, the two heavy chains of the first immunotherapeutic are covalently crosslinked with a first two disulfide bonds, and the two heavy chains of the second immunotherapeutic are covalently crosslinked with a second two disulfide bonds. The disulfide bonds that covalently crosslink two heavy chains are typically disulfide bonds of the IgG hinge region. The two heavy chains of the first immunotherapeutic and/or the two heavy chains of the second immunotherapeutic are not necessarily crosslinked with the first one or more disulfide bond(s) and the second one or more disulfide bond(s), respectively, for example, because the first immunotherapeutic and/or the second immunotherapeutic may be provided under mild reducing conditions.

In some embodiments, (a) the first immunotherapeutic comprises a first IgG with two heavy chains that have a first amino acid sequence; (b) the second immunotherapeutic comprises a second IgG with two heavy chains that have a second amino acid sequence; (c) the first amino acid sequence includes a mutation of a native amino acid to a cysteine; (d) the second amino acid sequence lacks the mutation; (e) the two heavy chains of the first immunotherapeutic are covalently crosslinked with a first one or more disulfide bond(s); and (f) the two heavy chains of the second immunotherapeutic are covalently crosslinked with a second one or more disulfide bond(s).

In some embodiments, (a) the first immunotherapeutic comprises a first IgG with two light chains that have a first light chain amino acid sequence; (b) the second immunotherapeutic comprises a second IgG with two light chains that have a second light chain amino acid sequence; (c) the first light chain amino acid sequence includes a mutation of a native amino acid to a cysteine; (d) the second light chain amino acid sequence lacks the mutation; (e) the two heavy chains of the first immunotherapeutic are covalently crosslinked with a first one or more disulfide bond(s); and (f) the two heavy chains of the second immunotherapeutic are covalently crosslinked with a second one or more disulfide bond(s).

In some embodiments, the method comprises incubating a solution comprising the first immunotherapeutic and the second immunotherapeutic under reducing conditions to reduce the first one or more disulfide bond(s) and the second one or more disulfide bond(s). In some specific embodiments, the reducing conditions comprise inclusion of one or more of beta-mercaptoethanol, molecular cysteine, cysteamine, and glutathione in the solution. In some very specific embodiments, the reducing conditions comprise inclusion of cysteamine in the solution.

In some embodiments, the method comprises incubating the solution under reducing conditions such that (a) the two heavy chains of the first immunotherapeutic dissociate to result in a half molecule of the first immunotherapeutic and (b) the two heavy chains of the second immunotherapeutic dissociate to result in half molecules of the second immunotherapeutic. In some specific embodiments, the method comprises incubating the solution under reducing conditions such that (a) the two heavy chains of the first immunotherapeutic dissociate to result in half molecules of the first immunotherapeutic and (b) the two heavy chains of the second immunotherapeutic dissociate to result in half molecules of the second immunotherapeutic, wherein the first immunotherapeutic refers to a single molecule of the first immunotherapeutic and the second immunotherapeutic refers to a single molecule of the second immunotherapeutic. The solution may optionally comprise additional molecules of one or both of the first immunotherapeutic and the second immunotherapeutic that optionally also dissociate, and, in practice, the solution generally comprises additional molecules of the first immunotherapeutic and the second immunotherapeutic, which include molecules of the first immunotherapeutic and the second immunotherapeutic that also dissociate.

When the two heavy chains of the first immunotherapeutic dissociate, then the two light chains of the first immunotherapeutic, each of which is typically covalently attached to a single heavy chain, dissociate along with the heavy chain to which it is attached. Each of the two light chains of the first immunotherapeutic is typically covalently attached to a single heavy chain, and the reducing conditions of this disclosure may advantageously be mild enough to preserve this covalent attachment.

When the two heavy chains of the second immunotherapeutic dissociate, then the two light chains of the second immunotherapeutic, each of which is typically covalently attached to a single heavy chain, dissociate along with the heavy chain to which it is attached. Each of the two light chains of the second immunotherapeutic is typically covalently attached to a single heavy chain, and the reducing conditions of this disclosure may advantageously be mild enough to preserve this covalent attachment.

In some embodiments, the method comprises incubating the solution under reducing conditions such that (a) at least a portion of the two heavy chains of the first immunotherapeutic dissociates to result in half molecules of the first immunotherapeutic and (b) at least a portion of the two heavy chains of the second immunotherapeutic dissociates to result in half molecules of the second immunotherapeutic. In some specific embodiments, the method comprises incubating the solution under reducing conditions such that (a) at least a portion of the two heavy chains of the first immunotherapeutic dissociates to result in half molecules of the first immunotherapeutic and (b) at least a portion of the two heavy chains of the second immunotherapeutic dissociates to result in half molecules of the second immunotherapeutic, wherein the first immunotherapeutic refers to a plurality of molecules of the first immunotherapeutic such that at least a portion of the plurality of molecules of the first immunotherapeutic have two heavy chains that dissociate; and the second immunotherapeutic refers to a plurality of molecules of the second immunotherapeutic such that at least a portion of the plurality of molecules of the second immunotherapeutic have two heavy chains that dissociate.

In some embodiments, the method comprises incubating the solution under reducing conditions such that a half molecule of the first immunotherapeutic recombines with a half molecule of the second immunotherapeutic to result in a chimeric immunotherapeutic, which is chimeric at least because it comprises both (i) a heavy chain from the first IgG, which comprises the cysteine, and (ii) a heavy chain from the second IgG, which lacks the cysteine. In some specific embodiments, the method comprises incubating the solution under reducing conditions such that a half molecule of the first immunotherapeutic recombines with a half molecule of the second immunotherapeutic to result in a chimeric immunotherapeutic, which is chimeric at least because it comprises both (i) a heavy chain from the first IgG, which comprises the cysteine, and (ii) a heavy chain from the second IgG, which lacks the cysteine, wherein the first immunotherapeutic refers to a single molecule of the first immunotherapeutic; the second immunotherapeutic refers to a single molecule of the second immunotherapeutic; the half molecule of the first immunotherapeutic refers to a single half molecule of the first immunotherapeutic; the half molecule of the second immunotherapeutic refers to a single half molecule of the second immunotherapeutic; and the chimeric immunotherapeutic refers to a single molecule of the chimeric immunotherapeutic. The term "the cysteine" refers to the cysteine of "a mutation of a native amino acid to a cysteine." The chimeric antibody also typically comprises (i) a light chain from the first IgG, which is covalently bound to the heavy chain from the first IgG, and (ii) a light chain from the second IgG, which is covalently bound to the heavy chain from the second IgG. Various methods of this disclosure require at least two chimeric immunotherapeutics, for example, to form a dimeric immunotherapeutic, and, in practice, the incubating step of this paragraph typically results in a plurality of molecules of the chimeric immunotherapeutic that comprise the chimeric immunotherapeutic.

In some embodiments, the method comprises incubating the solution under reducing conditions such that a half molecule of the first immunotherapeutic recombines with a half molecule of the second immunotherapeutic to result in a chimeric immunotherapeutic, which is chimeric at least because it comprises both (i) a light chain of the first IgG, which comprises the cysteine, and (ii) a light chain of the second IgG, which lacks the cysteine. In some specific embodiments, the method comprises incubating the solution under reducing conditions such that a half molecule of the first immunotherapeutic recombines with a half molecule of the second immunotherapeutic to result in a chimeric immunotherapeutic, which is chimeric at least because it comprises both (i) a light chain of the first IgG, which comprises the cysteine, and (ii) a light chain of the second IgG, which lacks the cysteine, wherein the first immunotherapeutic refers to a single molecule of the first immunotherapeutic; the second immunotherapeutic refers to a single molecule of the second immunotherapeutic; the half molecule of the first immunotherapeutic refers to a single half molecule of the first immunotherapeutic; the half molecule of the second immunotherapeutic refers to a single half molecule of the second immunotherapeutic; and the chimeric immunotherapeutic refers to a single molecule of the chimeric immunotherapeutic. The term "the cysteine" refers to the cysteine of "a mutation of a native amino acid to a cysteine." The chimeric antibody also comprises (i) a heavy chain from the first IgG, which is covalently bound to the light chain from the first IgG, and (ii) a heavy chain from the second IgG, which is covalently bound to the light chain from the second IgG. Various methods of this disclosure require at least two chimeric immunotherapeutics, for example, to form a dimeric immunotherapeutic, and, in practice, the incubating step of this paragraph typically results in a plurality of molecules of the chimeric immunotherapeutic that comprise the chimeric immunotherapeutic.

In some embodiments, the method comprises incubating the solution under reducing conditions such that at least a portion of the half molecule of the first immunotherapeutic recombines with at least a portion of the half molecule of the second immunotherapeutic to result in a chimeric immunotherapeutic, which is chimeric at least because it comprises both (i) a heavy chain from the first IgG, which comprises the cysteine, and (ii) a heavy chain from the second IgG, which lacks the cysteine. In some specific embodiments, the method comprises incubating the solution under reducing conditions such that at least a portion of the half molecule of the first immunotherapeutic recombines with at least a portion of the half molecule of the second immunotherapeutic to result in a chimeric immunotherapeutic, which is chimeric at least because it comprises both (i) a heavy chain from the first IgG, which comprises the cysteine, and (ii) a heavy chain from the second IgG, which lacks the cysteine, wherein the first immunotherapeutic refers to a plurality of molecules of the first immunotherapeutic; the second immunotherapeutic refers to a plurality of molecules of the second immunotherapeutic; the half molecule of the first immunotherapeutic refers to a plurality of half molecules of the first immunotherapeutic; the half molecule of the second immunotherapeutic refers to a plurality of half molecules of the second immunotherapeutic; and the chimeric immunotherapeutic refers to a plurality of molecules of the chimeric immunotherapeutic. The term "the cysteine" refers to the cysteine of "a mutation of a native amino acid to a cysteine." The chimeric antibody also typically comprises (i) a light chain from the first IgG, which is covalently bound to the heavy chain from the first IgG, and (ii) a light chain from the second IgG, which is covalently bound to the heavy chain from the second IgG.

In some embodiments, the method comprises incubating the solution under reducing conditions such that at least a portion of the half molecule of the first immunotherapeutic recombines with at least a portion of the half molecule of the second immunotherapeutic to result in a chimeric immunotherapeutic, which is chimeric at least because it comprises both (i) a light chain of the first IgG, which comprises the cysteine, and (ii) a light chain of the second IgG, which lacks the cysteine. In some specific embodiments, the method comprises incubating the solution under reducing conditions such that at least a portion of the half molecule of the first immunotherapeutic recombines with at least a portion of the half molecule of the second immunotherapeutic to result in a chimeric immunotherapeutic, which is chimeric at least because it comprises both (i) a light chain of the first IgG, which comprises the cysteine, and (ii) a light chain of the second IgG, which lacks the cysteine, wherein the first immunotherapeutic refers to a plurality of molecules of the first immunotherapeutic; the second immunotherapeutic refers to a plurality of molecules of the second immunotherapeutic; the half molecule of the first immunotherapeutic refers to a plurality of half molecules of the first immunotherapeutic; the half molecule of the second immunotherapeutic refers to a plurality of half molecules of the second immunotherapeutic; and the chimeric immunotherapeutic refers to a plurality of molecules of the chimeric immunotherapeutic. The term "the cysteine" refers to the cysteine of "a mutation of a native amino acid to a cysteine." The chimeric antibody also comprises (i) a heavy chain from the first IgG, which is covalently bound to the light chain of the first IgG, and (ii) a heavy chain from the second IgG, which is covalently bound to the light chain of the second IgG.

In some embodiments, the method comprises incubating a solution comprising the first immunotherapeutic and the second immunotherapeutic under reducing conditions to reduce the first one or more disulfide bond(s) and the second one or more disulfide bond(s) such that (a) the two heavy chains of the first immunotherapeutic dissociate to result in half molecules of the first immunotherapeutic; (b) the two heavy chains of the second immunotherapeutic dissociate to result in half molecules of the second immunotherapeutic; and (c) a half molecule of the first immunotherapeutic recombines with a half molecule of the second immunotherapeutic to result in a chimeric immunotherapeutic, which is chimeric at least because it comprises both (i) a heavy chain from the first IgG, which comprises the cysteine, and (ii) a heavy chain from the second IgG, which lacks the cysteine.

In some embodiments, the method comprises incubating a solution comprising the first immunotherapeutic and the second immunotherapeutic under reducing conditions to reduce the first one or more disulfide bond(s) and the second one or more disulfide bond(s) such that (a) the two heavy chains of the first immunotherapeutic dissociate to result in half molecules of the first immunotherapeutic; (b) the two heavy chains of the second immunotherapeutic dissociate to result in half molecules of the second immunotherapeutic; and (c) a half molecule of the first immunotherapeutic recombines with a half molecule of the second immunotherapeutic to result in a chimeric immunotherapeutic, which is chimeric at least because it comprises both (i) a light chain of the first IgG, which comprises the cysteine, and (ii) a light chain of the second IgG, which lacks the cysteine.

In some embodiments, the method comprises incubating a solution comprising the first immunotherapeutic and the second immunotherapeutic under reducing conditions to reduce the first one or more disulfide bond(s) and the second one or more disulfide bond(s) such that (a) at least a portion of the two heavy chains of the first immunotherapeutic dissociates to result in half molecules of the first immunotherapeutic; (b) at least a portion of the two heavy chains of the second immunotherapeutic dissociates to result in half molecules of the second immunotherapeutic; and (c) at least a portion of the half molecule of the first immunotherapeutic recombines with at least a portion of the half molecule of the second immunotherapeutic to result in a chimeric immunotherapeutic, which is chimeric at least because it comprises both (i) a heavy chain from the first IgG, which comprises the cysteine, and (ii) a heavy chain from the second IgG, which lacks the cysteine.

In some embodiments, the method comprises incubating a solution comprising the first immunotherapeutic and the second immunotherapeutic under reducing conditions to reduce the first one or more disulfide bond(s) and the second one or more disulfide bond(s) such that (a) at least a portion of the two heavy chains of the first immunotherapeutic dissociates to result in half molecules of the first immunotherapeutic; (b) at least a portion of the two heavy chains of the second immunotherapeutic dissociates to result in half molecules of the second immunotherapeutic; and (c) at least a portion of the half molecule of the first immunotherapeutic recombines with at least a portion of the half molecule of the second immunotherapeutic to result in a chimeric immunotherapeutic, which is chimeric at least because it comprises both (i) a light chain of the first IgG, which comprises the cysteine, and (ii) a light chain of the second IgG, which lacks the cysteine.

In some embodiments, the method comprises incubating the chimeric immunotherapeutic under oxidizing conditions to form one or more disulfide bond(s) between one or more cysteine(s) of the heavy chain from the first IgG of the chimeric immunotherapeutic and one or more cysteine(s) of the heavy chain from the second IgG of the chimeric immunotherapeutic, which one or more cysteine(s) of the heavy chain from the first IgG participated in the first one or more disulfide bond(s), and which one or more cysteine(s) of the heavy chain from the second IgG participated in the second one or more disulfide bond(s).

In this disclosure, "cysteine(s)" of "one or more cysteine(s)" (as in the preceding paragraph) do not comprise "the cysteine" of "a mutation of a native amino acid to a cysteine" because the "cysteine(s)" of "one or more cysteine(s)" refer to cysteine(s) that crosslink two half molecules of an IgG whereas "the cysteine" of "a mutation of a native amino acid to a cysteine" crosslinks two chimeric IgGs of a dimeric immunotherapeutic. "Molecular cysteine" does not form part of any amino acid sequence and may instead be dissolved in solution such that it exists, for example, as a zwitterion comprising ammonium and carboxylate groups.

In some embodiments, the method comprises incubating the chimeric immunotherapeutic under oxidizing conditions to form a disulfide bond between (a) the cysteine of the heavy chain from the first IgG of a first molecule of the chimeric immunotherapeutic and (b) the cysteine of the heavy chain from the first IgG of a second molecule of the chimeric immunotherapeutic to result in the dimeric immunotherapeutic.

In this disclosure, the terms "one or more disulfide bond(s)" and "disulfide bonds," plural, do not comprise the disulfide bond, singular (as in "a disulfide bond" of the preceding paragraph), because the disulfide bond(s) of "one or more disulfide bond(s)" and "disulfide bonds" refer to disulfide bonds that crosslink two half molecules of an IgG whereas "the disulfide bond" (as in "a disulfide bond" of the preceding paragraph) crosslinks two chimeric IgGs of a dimeric immunotherapeutic.

In some embodiments, the method comprises incubating the chimeric immunotherapeutic under oxidizing conditions to form a disulfide bond between (a) the cysteine of the light chain from the first IgG of a first molecule of the chimeric immunotherapeutic and (b) the cysteine of the light chain from the first IgG of a second molecule of the chimeric immunotherapeutic to result in the dimeric immunotherapeutic.

In some embodiments, (1) incubating the chimeric immunotherapeutic under oxidizing conditions to form one or more disulfide bond(s) between one or more cysteine(s) of the heavy chain from the first IgG of the chimeric immunotherapeutic and one or more cysteine(s) of the heavy chain from the second IgG of the chimeric immunotherapeutic, and (2) incubating the chimeric immunotherapeutic under oxidizing conditions to result in the dimeric immunotherapeutic constitutes the same incubating, for example, such that (1) the one or more disulfide bond(s) are formed and (2) the dimeric immunotherapeutic is produced in either order, concurrently, or in an order that cannot readily be distinguished.

In some embodiments, the first IgG specifically binds an antigen selected from 4-1BB, 5'-nucleotidase, 5T4, activin receptor-like kinase 1, alpha-fetoprotein, angiopoietin 2, AXL, B7-H3, B-cell activating factor (BAFF), B-cell maturation antigen (BCMA), B-cell receptor (BCR), c-Met, C242, CA-125, CanAg, carbonic anhydrase 9 (CA-IX), carcinoembryonic antigen, CCR4, CCR5, CD3, CD4, CD19, CD20, CD22, CD23, CD25, CD27, CD28, CD30, CD33, CD37, CD38, CD40, CD44, CD51, CD56, CD70, CD74, CD79B, CD80, CD123, CD134, CD152, CD200, CD276, CD319, CEACAM5, claudin 18, coagulation factor III, connective tissue growth factor (CTGF), colony stimulating factor 1 (CSF1), colony stimulating factor 1 receptor (CSFIR), colony stimulating factor 2 (CSF2), CTLA-4, CXCR4, dendritic cell-associated lectin 2, DLL3, DLL4, DR5, EGFL7, EGFR, endoglin, EpCAM, ephrin receptor A3 (EPHA3), epidermal growth factor receptor (EGFR), ERBB3 (HER3), ERB4, fibroblast activation protein alpha (FAP), FGFR2, fibronectin extra domain-B, folate hydrolase, folate receptor 1, Frizzled receptor, GD2 ganglioside, GD3 ganglioside, gelatinase B, glycoprotein 100 (gp100), glypican 3, GPNMB, G protein-coupled receptor 5D (GPRC5D), GUCY2C, hepatocyte growth factor (HGF), HER1, HER2, HGFR, histone complex, HLA-DR, human scatter factor receptor kinase, IGF-1 receptor (IGF-IR; CD221), IGF-2, interleukin 1 alpha, interleukin-2, interleukin-6, interleukin-13, integrin alph5beta1, integrin alphaVbeta3, KIR2D, LAG3, Lewis-Y antigen, LIV-1, LRRC15, macrophage migration inhibitory factor (MIF), MCP-1, melanoma cell adhesion molecule (MCAM), mesothelin, MUC1, MUC5AC, nectin-4, NGNA ganglioside, Notch 1, Notch receptor, NRP1, PCDC1, PD-1, PD-L1, PDGFRA, phosphate-sodium co-transporter, phosphatidylserine, PTK7, root plate-specific spondin 3, ROR1, SDC1, SLAMF7, SLITRK6, Sp17, STEAP1, syndecan 1, TEM1, tenascin C, TGF-beta, TIGIT, TRAIL-R1, TRAIL-R2, tumor-associated calcium signal transducer 2 (TROP-2), tumor antigen CTAA16.88, tumor-specific glycosylated MUC1, tumor-associated glycoprotein 72 (TAG-72), TWEAK receptor, TYRP1, VEGF-A, VEGFR-1, VEGFR-2, and vimentin. In some specific embodiments, the first IgG binds Sp17 (human sperm protein 17).

In some embodiments, the second IgG specifically binds an antigen set forth in the preceding paragraph.

The first IgG and the second IgG may bind the same or different antigen. In some specific embodiments, the first IgG and the second IgG bind the same antigen.

The first IgG and the second IgG may bind the same or different epitope of an antigen. In some specific embodiments, the first IgG and the second IgG bind the same epitope.

In some embodiments, (1) the first IgG has a first variable light domain complementarity-determining region 1 (VL CDR1) amino acid sequence, a first VL CDR2 amino acid sequence, a first VL CDR3 amino acid sequence, a first variable heavy domain CDR1 (VH CDR1) amino acid sequence, a first VH CDR2 amino acid sequence, and a first VH CDR3 amino acid sequence; (2) the second IgG has a second VL CDR1 amino acid sequence, a second VL CDR2 amino acid sequence, a second VL CDR3 amino acid sequence, a second VH CDR 1 amino acid sequence, a second VH CDR2 amino acid sequence, and a second VH CDR3 amino acid sequence; (3) the first VL CDR1 amino acid sequence and the second VL CDR1 amino acid sequence are identical; (4) the first VL CDR2 amino acid sequence and the second VL CDR2 amino acid sequence are identical; (5) the first VL CDR3 amino acid sequence and the second VL CDR3 amino acid sequence are identical; (6) the first VH CDR1 amino acid sequence and the second VH CDR1 amino acid sequence are identical; (7) the first VH CDR2 amino acid sequence and the second VH CDR2 amino acid sequence are identical; and (8) the first VH CDR3 amino acid sequence and the second VH CDR3 amino acid sequence are identical.

In some embodiments, (1) the first IgG has a first light chain variable domain amino acid sequence and a first heavy chain variable domain amino acid sequence; (2) the second IgG has a second light chain variable domain amino acid sequence and a second heavy chain variable domain amino acid sequence; (3) the first light chain variable domain amino acid sequence and the second light chain variable domain amino acid sequence are identical; and (4) the first heavy chain variable domain amino acid sequence and the second heavy chain variable domain amino acid sequence are identical.

In some embodiments, (1) the solution comprises a molar concentration of each of a reducing agent, the first immunotherapeutic, and the second immunotherapeutic; (2) the solution comprises a combined molar concentration of the first immunotherapeutic and the second immunotherapeutic, which is equal to the sum of the molar concentration of the first immunotherapeutic and the molar concentration of the second immunotherapeutic; and (3) the molar concentration of the reducing agent is greater than the combined molar concentration. In some specific embodiments, the molar concentration of the reducing agent is at least two times greater than the combined molar concentration (for example, the combined molar concentration is 7.5 millimolar and the molar concentration of the reducing agent is at least 15 millimolar). In some very specific embodiments, the molar concentration of the reducing agent is at least four times greater than the combined molar concentration (for example, the combined molar concentration is 7.5 millimolar and the molar concentration of the reducing agent is at least 30 millimolar).

In some embodiments, the reducing agent is selected from beta-mercaptoethanol, molecular cysteine, cysteamine, and glutathione. In some specific embodiments, the reducing agent is cysteamine.

In some embodiments, the concentration of the reducing agent is at least 5 millimolar and up to than 750 millimolar. In some specific embodiments, the concentration of the reducing agent is at least 10 millimolar and up to 500 millimolar. In some very specific embodiments, the concentration of the reducing agent is at least 25 millimolar and up to 250 millimolar.

In some embodiments, the method comprises purifying the chimeric immunotherapeutic, wherein (1) the solution comprises a reducing agent; and (2) the purifying separates the chimeric immunotherapeutic from the reducing agent. In some specific embodiments, the method comprises purifying the chimeric immunotherapeutic, wherein (1) the solution comprises a reducing agent; (2) the purifying separates the chimeric immunotherapeutic from the reducing agent; and (3) incubating the chimeric immunotherapeutic under oxidizing conditions comprises the purifying.

Purification methods are not limiting. In some embodiments, the purifying is selected from dialysis, protein A purification, protein G purification, protein A/G purification, protein L purification, ammonium sulfate precipitation, size exclusion chromatography, ion exchange chromatography, affinity chromatography, hydrophobic interaction chromatography, thiophilic absorption, and immobilized metal chelate chromatography.

In some embodiments, purifying the chimeric immunotherapeutic and incubating the chimeric immunotherapeutic under oxidizing conditions are performed simultaneously. For example, the purifying may expose the chimeric immunotherapeutic to oxidizing conditions.

In some embodiments, incubating the chimeric immunotherapeutic under oxidizing conditions comprises incubating the chimeric immunotherapeutic at a pH of at least 7.0. In some specific embodiments, incubating the chimeric immunotherapeutic under oxidizing conditions comprises incubating the chimeric immunotherapeutic at a pH of at least 7.0 and up to a pH of 8.0. In some very specific embodiments, incubating the chimeric immunotherapeutic under oxidizing conditions comprises incubating the chimeric immunotherapeutic at a pH of at least 7.2 and up to a pH of 7.8. Incubating the chimeric immunotherapeutic at a pH of at least 7.0 may be sufficient oxidizing conditions, for example, in the presence of dissolved oxygen, because such conditions deprotonate cysteines.

In some embodiments, the first IgG is a human IgG1, the native amino acid is S444, and the mutation is S444C. In some specific embodiments, the first IgG is a human IgG1; the native amino acid is S444; the mutation is S444C; and the first IgG optionally comprises one or more further substitutions, deletions, and/or insertions.

In this disclosure, the amino acid positions of an IgG are defined according to EU numbering as set forth in Kabat, E. A. et al., "Sequences of proteins of immunological interest." 5th Edition-US Department of Health and Human Services, NIH publication No. 91-3242 (1991) (hereinafter, "Kabat"), which is incorporated by reference in its entirety.

In some embodiments, the first IgG is a human IgG1, the native amino acid is S119, and the mutation is S119C. In some specific embodiments, the first IgG is a human IgG1;

the native amino acid is S119; the mutation is S119C; and the first IgG optionally comprises one or more further substitutions, deletions, and/or insertions.

S119C and S444C are representative mutations to native amino acids that are known to crosslink IgG1 antibodies with high efficiency. Other suitable native amino acids may be identified by analyzing a crystal structure of an IgG, for example, to identify native amino acids that display solvent-accessible surface areas that are greater than the solvent-accessible surface areas of buried native amino acids. Other suitable native amino acids may include, for example, asparagine amino acids that might otherwise be glycosylated. Other suitable native amino acids may include, for example, (1) alanine amino acids that have a greater solvent-accessible surface area than other alanine amino acids of an IgG, (2) serine amino acids, (3) threonine amino acids, (4) aspartate amino acids, (5) glutamate amino acids, (6) asparagine amino acids, (7) glutamine amino acids, (8) histidine amino acids, (8) arginine amino acids, (9) lysine amino acids, (10) methionine amino acids, and (11) tyrosine amino acids; the scope of suitable native amino acids is nevertheless not limiting and even hydrophobic amino acids may be suitable native amino acids if a hydrophobic amino acid displays a significant solvent-accessible surface area.

In some embodiments, the first IgG is a human IgG1, and the first IgG comprises a mutation to F405 and also comprises one or more further substitutions, deletions, and/or insertions that include the mutation of the native amino acid to the cysteine. In some specific embodiments, the mutation is selected from F405A, F405D, F405E, F405G, F405H, F405I, F405K, F405L, F405M, F405N, F405Q, F405S, F405T, F405V, F405W, and F405Y. In some very specific embodiments, the mutation is F405L.

In some embodiments, the first IgG is a human IgG1, and the first IgG comprises one, two, three, or four mutation(s) to one, two, three, or each of L368, D399, F405, and Y407 and also comprises one or more further substitutions, deletions, and/or insertions that include the mutation of the native amino acid to the cysteine. In some specific embodiments, the mutation(s) are selected from L368A, L368D, L368E, L368G, L368H, L368I, L368N, L368Q, L368R, L368S, L368T, L368V, L368W, D399A, D399F, D399H, D399K, D399R, D399Y, F405A, F405D, F405E, F405G, F405H, F405I, F405K, F405L, F405M, F405N, F405Q, F405S, F405T, F405V, F405W, F405Y, Y407G, Y407L, Y407M, and Y407W.

In some embodiments, the second IgG is a human IgG1, and the second IgG comprises a mutation to K409 and optionally also comprises one or more further substitutions, deletions, and/or insertions. In some specific embodiments, the mutation is selected from K409A, K409C, K409D, K409E, K409F, K409G, K409H, K409I, K409N, K409P, K409Q, K409R, K409S, K409T, K409V, K409W, and K409Y. In some very specific embodiments, the mutation is K409R.

In some embodiments, the first IgG is a human IgG1; the first IgG comprises a mutation to F405 and also comprises one or more further substitutions, deletions, and/or insertions that include the mutation of the native amino acid to the cysteine; the second IgG is a human IgG1; and the second IgG comprises a mutation to K409 and optionally also comprises one or more further substitutions, deletions, and/or insertions. In some specific embodiments, the mutation to F405 is selected from F405A, F405D, F405E, F405G, F405H, F405I, F405K, F405L, F405M, F405N, F405Q, F405S, F405T, F405V, F405W, and F405Y; and the mutation to K409 is selected from K409A, K409C, K409D, K409E, K409F, K409G, K409H, K409I, K409N, K409P, K409Q, K409R, K409S, K409T, K409V, K409W, and K409Y. In some very specific embodiments, the mutation to F405 is F405L, and the mutation to K409 is K409R.

In some embodiments, the first IgG is a human IgG1; the first IgG comprises one, two, three, or four mutation(s) to one, two, three, or each of L368, D399, F405, and Y407 and also comprises one or more further substitutions, deletions, and/or insertions that include the mutation of the native amino acid to the cysteine; the second IgG is a human IgG1; and the second IgG comprises a mutation to K409 and optionally also comprises one or more further substitutions, deletions, and/or insertions. In some specific embodiments, the mutation(s) to one, two, three, or each of L368, D399, F405, and Y407 are selected from L368A, L368D, L368E, L368G, L368H, L368I, L368N, L368Q, L368R, L368S, L368T, L368V, L368W, D399A, D399F, D399H, D399K, D399R, D399Y, F405A, F405D, F405E, F405G, F405H, F405I, F405K, F405L, F405M, F405N, F405Q, F405S, F405T, F405V, F405W, F405Y, Y407G, Y407L, Y407M, and Y407W; and the mutation to K409 is selected from K409A, K409C, K409D, K409E, K409F, K409G, K409H, K409I, K409N, K409P, K409Q, K409R, K409S, K409T, K409V, K409W, and K409Y. In some very specific embodiments, the mutation(s) to one, two, three, or each of L368, D399, F405, and Y407 comprise F405L, and the mutation to K409 is K409R.

In some embodiments, the first IgG is a human IgG1, and the first IgG comprises a mutation to K409 and also comprises one or more further substitutions, deletions, and/or insertions that include the mutation of the native amino acid to the cysteine. In some specific embodiments, the mutation is selected from K409A, K409C, K409D, K409E, K409F, K409G, K409H, K409I, K409N, K409P, K409Q, K409R, K409S, K409T, K409V, K409W, and K409Y. In some very specific embodiments, the mutation is K409R.

In some embodiments, the second IgG is a human IgG1, and the second IgG comprises a mutation to F405 and optionally also comprises one or more further substitutions, deletions, and/or insertions. In some specific embodiments, the mutation is selected from F405A, F405D, F405E, F405G, F405H, F405I, F405K, F405L, F405M, F405N, F405Q, F405S, F405T, F405V, F405W, and F405Y. In some very specific embodiments, the mutation is F405L.

In some embodiments, the second IgG is a human IgG1, and the second IgG comprises one, two, three, or four mutation(s) to one, two, three, or each of L368, D399, F405, and Y407 and optionally also comprises one or more further substitutions, deletions, and/or insertions. In some specific embodiments, the mutation(s) are selected from L368A, L368D, L368E, L368G, L368H, L368I, L368N, L368Q, L368R, L368S, L368T, L368V, L368W, D399A, D399F, D399H, D399K, D399R, D399Y, F405A, F405D, F405E, F405G, F405H, F405I, F405K, F405L, F405M, F405N, F405Q, F405S, F405T, F405V, F405W, F405Y, Y407G, Y407L, Y407M, and Y407W.

In some embodiments, the first IgG is a human IgG1; the first IgG comprises a mutation to K409 and also comprises one or more further substitutions, deletions, and/or insertions that include the mutation of the native amino acid to the cysteine; the second IgG is a human IgG1; and the second IgG comprises a mutation to F405 and optionally also comprises one or more further substitutions, deletions, and/or insertions. In some specific embodiments, the mutation to K409 is selected from K409A, K409C, K409D, K409E, K409F, K409G, K409H, K409I, K409N, K409P, K409Q, K409R, K409S, K409T, K409V, K409W, and K409Y; and the mutation to F405 is selected from F405A, F405D, F405E, F405G, F405H, F405I, F405K, F405L, F405M, F405N, F405Q, F405S, F405T, F405V, F405W, and F405Y. In some very specific embodiments, the mutation to K409 is K409R, and the mutation to F405 is F405L.

In some embodiments, the first IgG is a human IgG1; the first IgG comprises a mutation to K409 and also comprises one or more further substitutions, deletions, and/or insertions that include the mutation of the native amino acid to the cysteine; the second IgG is a human IgG1; and the second IgG comprises one, two, three, or four mutation(s) to one, two, three, or each of L368, D399, F405, and Y407 and optionally also comprises one or more further substitutions, deletions, and/or insertions. In some specific embodiments, the mutation to K409 is selected from K409A, K409C, K409D, K409E, K409F, K409G, K409H, K409I, K409N, K409P, K409Q, K409R, K409S, K409T, K409V, K409W, and K409Y; and the mutation(s) to one, two, three, or each of L368, D399, F405, and Y407 are selected from L368A, L368D, L368E, L368G, L368H, L368I, L368N, L368Q, L368R, L368S, L368T, L368V, L368W, D399A, D399F, D399H, D399K, D399R, D399Y, F405A, F405D, F405E, F405G, F405H, F405I, F405K, F405L, F405M, F405N, F405Q, F405S, F405T, F405V, F405W, F405Y, Y407G, Y407L, Y407M, and Y407W. In some very specific embodiments, the mutation to K409 is K409R, and the mutation(s) to one, two, three, or each of L368, D399, F405, and Y407 comprise F405L.

In some embodiments, the first IgG has a lysine at amino acid position 409 and the second IgG has an arginine at amino acid position 409.

In some embodiments, the first IgG has a phenylalanine at amino acid position 405 and the second IgG has a leucine at amino acid position 405.

In some embodiments, the first IgG has a lysine at amino acid position 409 and a phenylalanine at amino acid position 405, and the second IgG has an arginine at amino acid position 409 and a leucine at amino acid position 405.

In some embodiments, the first IgG has an arginine at amino acid position 409 and the second IgG has a lysine at amino acid position 409.

In some embodiments, the first IgG has a leucine at amino acid position 405 and the second IgG has a phenylalanine at amino acid position 405.

In some embodiments, the first IgG has an arginine at amino acid position 409 and a leucine at amino acid position 405, and the second IgG has a lysine at amino acid position 409 and a phenylalanine at amino acid position 405.

In some embodiments, the first IgG is a human IgG1; the second IgG is a human IgG1; and either (a) both (i) the first IgG comprises a F405L mutation, and (ii) the second IgG comprises a K409R mutation or (b) both (i) the first IgG comprises a K409R mutation, and (ii) the second IgG comprises a F405L mutation.

Other non-limiting examples mutations that may be made to one or both of the first IgG and the second IgG are set forth, for example, in U.S. Pat. No. 5,731,168 (Genentech), U.S. Pat. No. 8,592,562 (Amgen), U.S. Pat. No. 9,505,848 (Merck), U.S. Pat. No. 10,011,858 (Chugai), and U.S. Pat. No. 10,597,464 (Genmab), which are incorporated by reference in their entireties.

Various aspects of this disclosure relate to a dimeric immunotherapeutic produced according to a method described herein. Such dimeric immunotherapeutics comprise two chimeric immunotherapeutics as described herein, which are crosslinked with a disulfide bond.

Various aspects of this disclosure relate to a chimeric immunotherapeutic produced according to a method described herein, which includes the mutation of the native amino acid to a cysteine.

Various aspects of this disclosure relate to a dimeric immunotherapeutic, comprising a first chimeric immunotherapeutic and a second chimeric immunotherapeutic. In some embodiments, the first chimeric immunotherapeutic and the second chimeric immunotherapeutic have identical amino acid sequences. The first chimeric immunotherapeutic and the second chimeric immunotherapeutic may nevertheless vary, for example, as a result of post-translational modifications such by heterogenous glycosylation patterns as well as heterogeneity in any chemical conjugation for chimeric immunotherapeutics that are immunoconjugates. The first chimeric immunotherapeutic and the second chimeric immunotherapeutic are "chimeric" because they are prepared from "half molecules" from two different immunotherapeutics as described herein (for example, a first immunotherapeutic and a second immunotherapeutic).

In some embodiments, (1) the first chimeric immunotherapeutic comprises a first chimeric IgG that comprises a first light chain, a first heavy chain, a second light chain, and a second heavy chain, which each have an amino acid sequence; (2) the second chimeric immunotherapeutic comprises a second chimeric IgG that comprises a first light chain, a first heavy chain, a second light chain, and a second heavy chain, which each have an amino acid sequence; (3) the amino acid sequences of the first light chain of the first chimeric IgG and the first light chain of the second chimeric IgG are identical; (4) the amino acid sequences of the second light chain of the first chimeric IgG and the second light chain of the second chimeric IgG are identical; (5) the amino acid sequences of the first heavy chain of the first chimeric IgG and the first heavy chain of the second chimeric IgG are identical; (6) the amino acid sequences of the second heavy chain of the first chimeric IgG and the second heavy chain of the second chimeric IgG are identical; (7) the amino acid sequences of the first heavy chain of the first chimeric IgG and the first heavy chain of the second chimeric IgG each include a mutation of a native amino acid to a cysteine; (8) the cysteine of the amino acid sequence of the first heavy chain of the first chimeric IgG and the cysteine of the amino acid sequence of the first heavy chain of the second chimeric IgG form a disulfide bond with each other; (9) the amino acid sequences of the second heavy chain of the first chimeric IgG and the second heavy chain of the second chimeric IgG each lack the mutation; (10) the first chimeric immunotherapeutic is chimeric at least because the amino acid sequence of the first heavy chain of the first chimeric IgG comprises the mutation and the amino acid sequence of the second heavy chain of the first chimeric IgG lacks the mutation such that the first chimeric IgG comprises two different heavy chains; and (11) the second chimeric immunotherapeutic is chimeric at least because the amino acid sequence of the first heavy chain of the second chimeric IgG comprises the mutation and the amino acid sequence of the second heavy chain of the second chimeric IgG lacks the mutation such that the second chimeric IgG comprises two different heavy chains.

In some embodiments, (1) the first chimeric immunotherapeutic comprises a first chimeric IgG that comprises a first light chain, a first heavy chain, a second light chain, and a second heavy chain, which each have an amino acid sequence; (2) the second chimeric immunotherapeutic comprises a second chimeric IgG that comprises a first light chain, a first heavy chain, a second light chain, and a second heavy chain, which each have an amino acid sequence; (3) the amino acid sequences of the first light chain of the first chimeric IgG and the first light chain of the second chimeric IgG are identical; (4) the amino acid sequences of the second light chain of the first chimeric IgG and the second light chain of the second chimeric IgG are identical; (5) the amino acid sequences of the first heavy chain of the first chimeric IgG and the first heavy chain of the second chimeric IgG are identical; (6) the amino acid sequences of the second heavy chain of the first chimeric IgG and the second heavy chain of the second chimeric IgG are identical; (7) the amino acid sequences of the first light chain of the first chimeric IgG and the first light chain of the second chimeric IgG each include a mutation of a native amino acid to a cysteine; (8) the cysteine of the amino acid sequence of the first light chain of the first chimeric IgG and the cysteine of the amino acid sequence of the first light chain of the second chimeric IgG form a disulfide bond; (9) the amino acid sequences of the second light chain of the first chimeric IgG and the second light chain of the second chimeric IgG each lack the mutation; (10) the first chimeric immunotherapeutic is chimeric at least because the amino acid sequence of the first light chain of the first chimeric IgG comprises the mutation and the amino acid sequence of the second light chain of the first chimeric IgG lacks the mutation such that the first chimeric IgG comprises two different light chains; and (11) the second chimeric immunotherapeutic is chimeric at least because the amino acid sequence of the first light chain of the second chimeric IgG comprises the mutation and the amino acid sequence of the second light chain of the second chimeric IgG lacks the mutation such that the second chimeric IgG comprises two different light chains.

In some embodiments, the first chimeric IgG and the second chimeric IgG are both chimeric human IgG1s; the native amino acid is S444; and the mutation is S444C.

In some embodiments, the first chimeric IgG and the second chimeric IgG are both chimeric human IgG1s; the native amino acid is S119; and the mutation is S119C.

In some embodiments, the first chimeric IgG and the first heavy chain of the second chimeric IgG each include a F405L mutation. In some embodiments, the amino acid sequences of the second heavy chain of the first chimeric IgG and the second heavy chain of the second chimeric IgG each include a K409R mutation. In some specific embodiments, the amino acid sequences of the first heavy chain of the first chimeric IgG and the first heavy chain of the second chimeric IgG each include a F405L mutation; and the amino acid sequences of the second heavy chain of the first chimeric IgG and the second heavy chain of the second chimeric IgG each include a K409R mutation.

In some embodiments, the amino acid sequences of the first heavy chain of the first chimeric IgG and the first heavy chain of the second chimeric IgG each include a K409R mutation. In some embodiments, the amino acid sequences of the second heavy chain of the first chimeric IgG and the second heavy chain of the second chimeric IgG each include a F405L mutation. In some specific embodiments, the first chimeric IgG and the second chimeric IgG are both chimeric human IgG1s; the amino acid sequences of the first heavy chain of the first chimeric IgG and the first heavy chain of the second chimeric IgG each include a K409R mutation; and the amino acid sequences of the second heavy chain of the first chimeric IgG and the second heavy chain of the second chimeric IgG each include a F405L mutation.

In some embodiments, the first heavy chain of the first chimeric IgG, the second heavy chain of the first chimeric IgG, the first heavy chain of the second chimeric IgG, and the second heavy chain of the second chimeric IgG each comprise a heavy chain variable region that has an identical amino acid sequence; and the first light chain of the first chimeric IgG, the second light chain of the first chimeric IgG, the first light chain of the second chimeric IgG, and the second light chain of the second chimeric IgG each comprise a light chain variable region that has an identical amino acid sequence.

In some embodiments, the first chimeric IgG and the second chimeric IgG are both chimeric human IgG1s; the native amino acid is S444; the mutation is S444C; the amino acid sequences of the first heavy chain of the first chimeric IgG and the first heavy chain of the second chimeric IgG each include a F405L mutation; the amino acid sequences of the second heavy chain of the first chimeric IgG and the second heavy chain of the second chimeric IgG each include a K409R mutation; the first heavy chain of the first chimeric IgG, the second heavy chain of the first chimeric IgG, the first heavy chain of the second chimeric IgG, and the second heavy chain of the second chimeric IgG each comprise a heavy chain variable region that has an identical amino acid sequence; and the first light chain of the first chimeric IgG, the second light chain of the first chimeric IgG, the first light chain of the second chimeric IgG, and the second light chain of the second chimeric IgG each comprise a light chain variable region that has an identical amino acid sequence.

In some embodiments, the amino acid sequences of the first light chain of the first chimeric immunotherapeutic, the second light chain of the first chimeric immunotherapeutic, the first light chain of the second chimeric immunotherapeutic, and the second light chain of the second chimeric immunotherapeutic are identical.

In some embodiments, the amino acid sequences of the first heavy chain of the first chimeric immunotherapeutic, the second heavy chain of the first chimeric immunotherapeutic, the first heavy chain of the second chimeric immunotherapeutic, and the second heavy chain of the second chimeric immunotherapeutic are identical.

In some embodiments, the first heavy chain of the first chimeric IgG, the second heavy chain of the first chimeric IgG, the first heavy chain of the second chimeric IgG, and the second heavy chain of the second chimeric IgG each comprise a heavy chain variable region that has an identical amino acid sequence; and the first light chain of the first chimeric IgG, the second light chain of the first chimeric IgG, the first light chain of the second chimeric IgG, and the second light chain of the second chimeric IgG each comprise a light chain variable region that has an identical amino acid sequence.

In some embodiments, the first heavy chain of the first chimeric IgG, the second heavy chain of the first chimeric IgG, the first heavy chain of the second chimeric IgG, and the second heavy chain of the second chimeric IgG each comprise (i) a VH CDR1 region comprising an amino acid sequence that is identical to SEQ ID NO: 5, (ii) a VH CDR2 region comprising an amino acid sequence that is identical to SEQ ID NO: 6, and (iii) a VH CDR3 region comprising an amino acid sequence that is identical to SEQ ID NO: 7; and the first light chain of the first chimeric IgG, the second light chain of the first chimeric IgG, the first light chain of the second chimeric IgG, and the second light chain of the second chimeric IgG each comprise (i) a VL CDR 1 region comprising an amino acid sequence that is identical to SEQ ID NO: 8, (ii) a VL CDR2 region comprising an amino acid sequence that is identical to SEQ ID NO: 9, and (iii) a VL CDR3 region comprising an amino acid sequence that is identical to SEQ ID NO: 10.

In some embodiments, the first heavy chain of the first chimeric IgG, the second heavy chain of the first chimeric IgG, the first heavy chain of the second chimeric IgG, and the second heavy chain of the second chimeric IgG each comprise a heavy chain variable region that has at least 90 percent sequence identity to SEQ ID NO: 3; and the first light chain of the first chimeric IgG, the second light chain of the first chimeric IgG, the first light chain of the second chimeric IgG, and the second light chain of the second chimeric IgG each comprise a light chain variable region that has at least 90 percent sequence identity to SEQ ID NO: 4. In some specific embodiments, the first heavy chain of the first chimeric IgG, the second heavy chain of the first chimeric IgG, the first heavy chain of the second chimeric IgG, and the second heavy chain of the second chimeric IgG each comprise a heavy chain variable region that has at least 95 percent sequence identity to SEQ ID NO: 3; and the first light chain of the first chimeric IgG, the second light chain of the first chimeric IgG, the first light chain of the second chimeric IgG, and the second light chain of the second chimeric IgG each comprise a light chain variable region that has at least 95 percent sequence identity to SEQ ID NO: 4. In some very specific embodiments, the first heavy chain of the first chimeric IgG, the second heavy chain of the first chimeric IgG, the first heavy chain of the second chimeric IgG, and the second heavy chain of the second chimeric IgG each comprise a heavy chain variable region that has SEQ ID NO: 3; and the first light chain of the first chimeric IgG, the second light chain of the first chimeric IgG, the first light chain of the second chimeric IgG, and the second light chain of the second chimeric IgG each comprise a light chain variable region that has SEQ ID NO: 4.

Having described various features of this disclosure both generally and specifically in the preceding detailed description, the following exemplification provides a specific example of the preparation of a dimeric immunotherapeutic as described herein. By way of this example, and in the context of the preceding detailed description, the skilled person will immediately recognize variations to the method set forth in the example (such as by selecting a different first IgG and/or a different second IgG). The following exemplification is illustrative only and shall not limit this disclosure or any patent claim that matures from this disclosure. Any patent claim that matures from this disclosure shall instead be limited by the explicit features recited in the claim in the context of its claim dependency and according to conventional principles of claim construction as applied in view of this disclosure.

Exemplification

The Example: A Method to Prepare Dimeric Immunotherapeutics

Figure 2A:
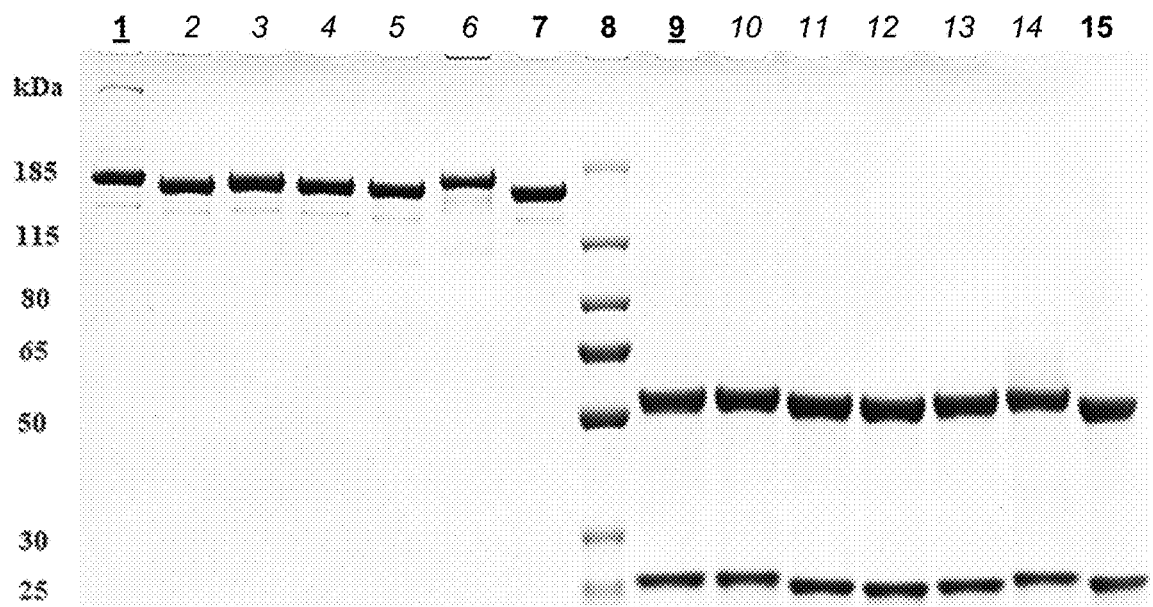
FIG. 2A is an image of a sodium dodecyl sulfate polyacrylamide gel electrophoresis (SDS-PAGE) gel of a first IgG used to manufacture a chimeric antibody of this disclosure, in which lane 1 was loaded with 1 microgram of the first IgG under non-reducing conditions, lane 7 was loaded with 1 microgram of a control IgG under non-reducing conditions, lane 8 was loaded with a molecular weight standard, lane 9 was loaded with 2 micrograms of the first IgG under reducing conditions, and lane 15 was loaded with 2 micrograms of the control IgG under reducing conditions.
Figure 2B:
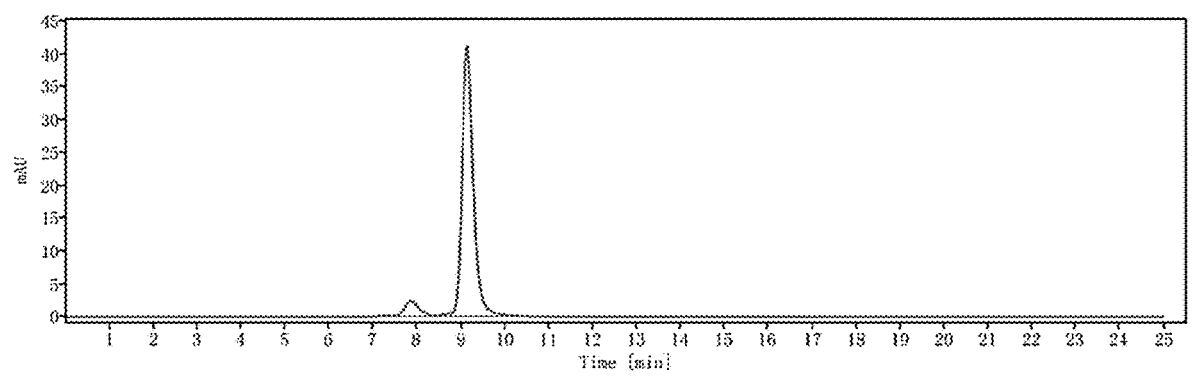
FIG. 2B is a chromatograph trace monitored at 280 nanometers for liquid chromatography performed on the first IgG, which suggests that the first IgG had a purity of about 91.96 percent.

A first IgG1 comprising F405L and S444C mutations was cloned, expressed, and purified. The positions of F405L and S444C are defined according to EU numbering as set forth in Kabat. An SDS-PAGE analysis of the first IgG1 is shown in FIG. 2A, in which lane 1 corresponds to 1 microgram of the first IgG1 loaded under non-reducing conditions, lane 7 corresponds to 1 microgram of an IgG standard loaded under non-reducing conditions, lane 8 corresponds to a molecular weight standard, lane 9 corresponds to 2 micrograms of the first IgG1 loaded under reducing conditions, and lane 15 corresponds to 2 micrograms of an IgG standard loaded under reducing conditions. The first IgG1 displayed a purity of about 91.96 percent as determined by liquid chromatography and shown in FIG. 2B.

The first IgG1 specifically binds Sp17. The nucleotide sequences encoding the heavy chain variable region and light chain variable regions of the first IgG1 antibody are set forth in SEQ ID NO: 1 & 2. These nucleotide sequences encode the amino acid sequences set forth in SEQ ID NO: 3 & 4, respectively. SEQ ID NO: 5 comprises the VH CDR1 region of the first IgG1. SEQ ID NO: 6 comprises the VH CDR2 region of the first IgG1. SEQ ID NO: 7 comprises the VH CDR3 region of the first IgG1. SEQ ID NO: 8 comprises the VL CDR1 region of the first IgG1. SEQ ID NO: 9 comprises the VL CDR2 region of the first IgG1. SEQ ID NO: 10 comprises the VL CDR3 region of the first IgG1.

TABLE 1

Nucleotide sequences of the VH and VL regions of an exemplary IgG

| SEQ ID NO: | Region | Sequence |
|---|---|---|
| 1 | VH | CAGGTACAGCTGCAGCAGTCAGGGGCTGAGGTGAAGAAGCCTGGGTCCTC GGTGAAGGTCTCCTGCAAGGCTTCTGGAGGCACCTTCAGCAGCTATGCTA TCAGCTGGGTGCGACAGGCCCCTGGACAAGGGCTTGAGTGGATGGGAAGG ATCATCCCTATCCTTGGTATAGCAAACTACGCACAGAAGTTCCAGGGCAG AGTCACGATTACCGCGGACAAATCCACGAGCACAGCCTACATGGAGCTGA GCAGCCTGAGATCTGAGGACACGGCCGTGTATTACTGTGCGAGACCCTCC GAAGAGGTGGTAGCTGCTTACGGTGCTTTTGATATCTGGGGCCAAGGGAC CACGGTCACCGTCTCAAGC |
| 2 | VL | GAAATTGTGCTGACTCAGTCTCCACTCTCCCTGCCCGTCAGACCTGGGGA GCCGGCCTCCATCTCCTGCAGGGCTAGTCAGAGCCTCCTGCGTAGTGACG GATTCAACTACTTGGATTGGTACCTGCAGAAGCCAGGGCAGTCTCCACAG CTCCTGGTCTATTTGGGTTCTAATCGGGCCTCCGGGGTCCCTGACAGGTT CAGTGGCAGTGGATCAGGCACAGATTTTACACTGAAAATCAGCAGAGTGG AGGCTGAGGATGTTGGGGTTTATTACTGCATGCAAGCTGTACAAACTCCG TACATTTTTGGCCAGGGGACCAAGCTGGAGATCAAA |

TABLE 2

Amino acid sequences of the VH and VL regions of an exemplary IgG

```
SEQ ID        Sequence  10        20        30        40
NO:    Region           1234567890123456789012345678901234567890

3    VH     QVQLQQSGAEVKKPGSSVKVSCKASGGTFSSYAISWVRQAPGOGLEWMGR
              IIPILGIANYAQKFQGRVTITADKSTSTAYMELSSLRSEDTAVYYCARPS
              EEVVAAYGAFDIWGQGTTVTVSS

4    VL     EIVLTQSPLSLPVRPGEPASISCRASQSLLRSDGFNYLDWYLQKPGOSPQ
              LLVYLGSNRASGVPDRFSGSGSGTDFTLKISRVEAEDVGVYYCMQAVQTP
              YIFGQGTKLEIK
```

TABLE 3

Amino acid sequences comprising CDRs of the VH and VL regions of an exemplary IgG

| SEQ ID NO: | Region | Sequence  10<br>12345678901234567 |
|---|---|---|
| 5 | VH CDR1 | GGTFSSYAIS |
| 6 | VH CDR2 | RIIPILGIANYAQKFQG |
| 7 | VH CDR3 | ARPSEEVVAAYGAFDI |
| 8 | VL CDR1 | RASQSLLRSDGFNYLD |
| 9 | VL CDR2 | LGSNRAS |
| 10 | VL CDR3 | MQAVQTPYIF |

Figure 3A:
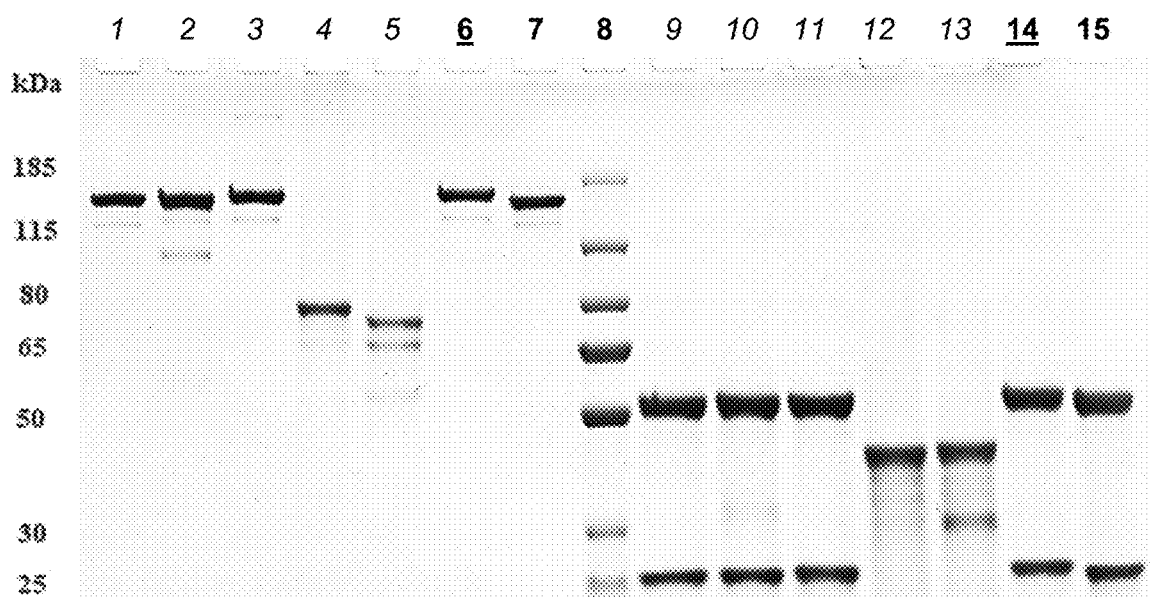
FIG. 3A is an image of an SDS-PAGE gel of a second IgG used to manufacture a chimeric antibody of this disclosure, in which lane 6 was loaded with 1 microgram of the second IgG under non-reducing conditions, lane 7 was loaded with 1 microgram of a control IgG under non-reducing conditions, lane 8 was loaded with a molecular weight standard, lane 14 was loaded with 2 micrograms of the second IgG under reducing conditions, and lane 15 was loaded with 2 micrograms of the control IgG under reducing conditions.
Figure 3B:
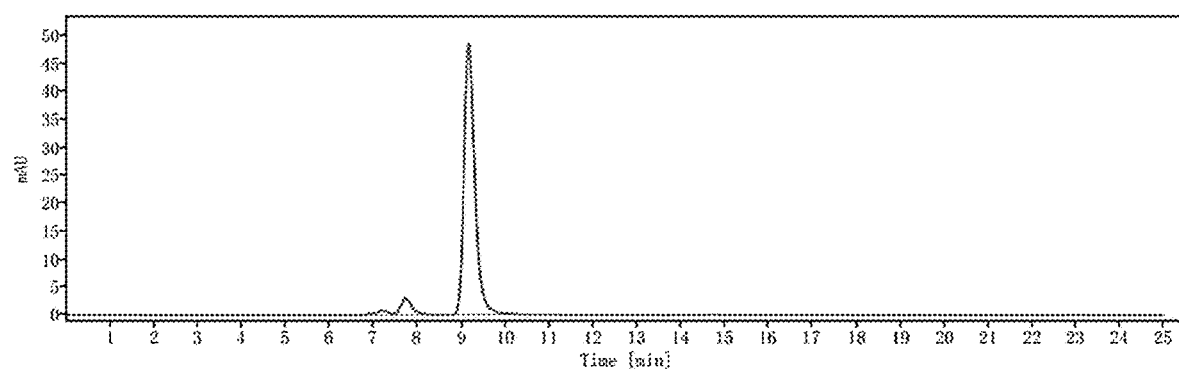
FIG. 3B is a chromatograph trace monitored at 280 nanometers for liquid chromatography performed on the second IgG, which suggests that the second IgG had a purity of about 92.39 percent.

A second IgG1 comprising a K409R mutation was cloned, expressed, and purified. The position of K409R is defined according to EU numbering as set forth in Kabat. An SDS-PAGE analysis of the second IgG1 is shown in FIG. 3A, in which lane 6 corresponds to 1 microgram of the second IgG1 loaded under non-reducing conditions, lane 7 corresponds to 1 microgram of an IgG standard loaded under non-reducing conditions, lane 8 corresponds to a molecular weight standard, lane 14 corresponds to 2 micrograms of the second IgG1 loaded under reducing conditions, and lane 15 corresponds to 2 micrograms of an IgG standard loaded under reducing conditions. The second IgG1 displayed a purity of about 92.39 percent as determined by liquid chromatography and shown in FIG. 3B.

The amino acid sequences of the first IgG1 and the second IgG1 were identical except for the F405L and S444C mutations of the first IgG1 and the K409R mutation of the second IgG1.

The second IgG1 specifically binds Sp17 and comprises the same variable regions as the first IgG1. The nucleotide sequences encoding the heavy chain variable region and light chain variable regions of the second IgG1 antibody are set forth in SEQ ID NO: 1 & 2. These nucleotide sequences encode the amino acid sequences set forth in SEQ ID NO: 3 & 4, respectively. SEQ ID NO: 5 comprises the VH CDR1 region of the second IgG1. SEQ ID NO: 6 comprises the VH CDR2 region of the second IgG1. SEQ ID NO: 7 comprises the VH CDR3 region of the second IgG1. SEQ ID NO: 8 comprises the VL CDR1 region of the second IgG1. SEQ ID NO: 9 comprises the VL CDR2 region of the second IgG1. SEQ ID NO: 10 comprises the VL CDR3 region of the second IgG1.

0.5 milligrams of the first IgG1 in 193.8 microliters and 0.5 milligrams of the second IgG1 in 204.9 microliters were combined, and then 44.3 microliters of 750 millimolar cysteamine was added to result in a reaction mixture with 443 microliters total volume containing 0.5 milligrams of the first IgG1 (about 7.5 millimolar), 0.5 milligrams of the second IgG1 (about 7.5 millimolar), and 75 millimolar cysteamine. The reaction mixture was incubated at 31 degrees Celsius for five hours to selectively reduce the disulfide bonds in the IgG1 hinge regions to allow for dissociation of the IgG1s into half molecules and recombination of the half molecules of the first IgG1 and the second IgG1 into chimeric IgGs. The F405L and K409R mutations favored dissociation of the half molecules of the first IgG1 and the second IgG1, respectively, and permitted recombination of the half molecules into chimeric IgG1s to drive an equilibrium that favored formation of chimeric IgG1s from half molecules of the first IgG1 and the second IgG1 rather than recombination of the half molecules back into the original first IgG1 and second IgG1.

Following the five hours, the reaction mixture was transferred into dialysis bags with a 10 kilodalton molecular weight cut-off (10 kDa MWCO), and the dialysis bags were transferred into 5 liters of phosphate-buffered saline (PBS) adjusted to a pH of 7.4. The first round of dialysis proceeded for four hours. The dialysis bags were then transferred into a fresh 5 liters of PBS (pH 7.4) and dialyzed overnight at 4 degrees Celsius. The slightly alkaline pH of 7.4 allowed for an equilibrium in which some cysteines of the chimeric IgG1s were deprotonated to allow for spontaneous oxidation of (1) cysteines in the hinge region of the chimeric IgG1 to form disulfide bonds that crosslink half molecules of the first IgG1 and the second IgG1 in the chimeric IgG1 and (2) the S444C cysteines of different chimeric IgG1s to form dimeric immunotherapeutics.

Following dialysis, the reaction mixture was transferred into microcentrifuge tubes, and 100 microliters of 100 millimolar cysteine was added to the reaction mixture to block remaining free cysteines. The blocked reaction mixture was then transferred back into dialysis bags with a 10 kDa MWCO, and the dialysis bags were transferred into 5 liters of 20 millimolar phosphate buffer (PB) adjusted to a pH of 6.0. The first round of dialysis proceeded for four hours, and then the dialysis bags were transferred into a fresh 5 liters of PB (pH 6.0) for a second four-hour round of dialysis.

Figure 4A:
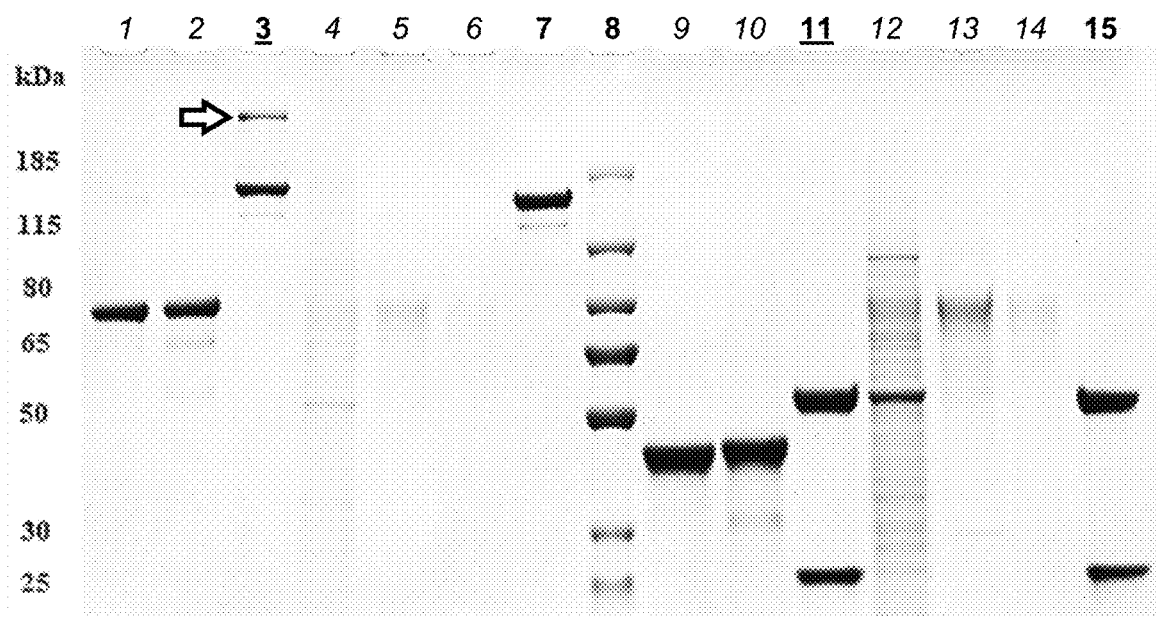
FIG. 4A is an image of an SDS-PAGE gel of monomers and dimers of a chimeric IgG of this disclosure, in which lane 3 was loaded with 1 microgram of the chimeric IgG under non-reducing conditions, lane 7 was loaded with 1 microgram of a control IgG under non-reducing conditions, lane 8 was loaded with a molecular weight standard, lane 11 was loaded with 2 micrograms of the chimeric IgG under reducing conditions, and lane 15 was loaded with 2 micrograms of the control IgG under reducing conditions. The arrow denotes dimers of the chimeric IgG visualized on the gel.
Figure 4B:
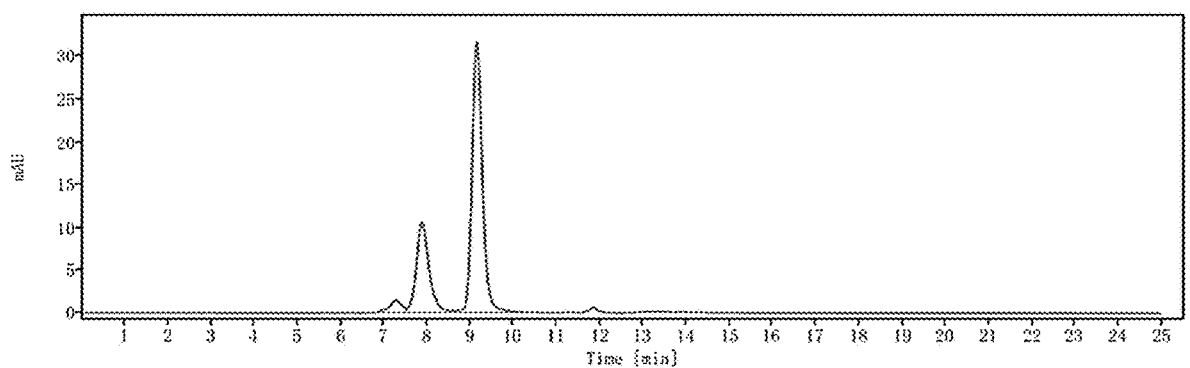
FIG. 4B is a chromatograph trace monitored at 280 nanometers for liquid chromatography performed on a reaction mixture used to prepare a dimeric immunotherapeutic of this disclosure. The chromatograph trace suggests that protein of the reaction mixture contains about 28.16 percent by mass of the dimeric immunotherapeutic.

An SDS-PAGE analysis of the reaction mixture is shown in FIG. 4A, in which lane 3 corresponds to 1 microgram of protein from the reaction mixture loaded under non-reducing conditions, lane 7 corresponds to 1 microgram of an IgG standard loaded under non-reducing conditions, lane 8 corresponds to a molecular weight standard, lane 11 corresponds to 2 micrograms of protein from the reaction mixture loaded under reducing conditions, and lane 15 corresponds to 2 micrograms of an IgG standard loaded under reducing conditions. The arrow in FIG. 4A depicts a protein band that displays a molecular weight that corresponds to the molecular weight of the dimeric immunotherapeutic. Liquid chromatography was used to determine that about 28.16 percent of the protein in the reaction mixture displayed a molecular weight consistent with the dimeric immunotherapeutic.

No patent claim that matures from this disclosure shall be interpreted as requiring any feature of the foregoing Exemplification. Any methods described in the claims or specification shall not be interpreted to require the steps to be performed in a specific order unless expressly stated otherwise. The methods shall be interpreted to provide support to perform the recited steps in any order unless expressly stated otherwise.

Certain features described in the context of separate implementations can also be implemented in combination in a single implementation. Conversely, various features that are described in the context of a single implementation can also be implemented in multiple implementations separately or in any suitable sub-combination. Moreover, although features may be described above in certain combinations and even initially claimed as such, one or more features from a claimed combination can be excised from the combination, and the claimed combination may be directed to a sub-combination or variation of a sub-combination.

The example configurations described in this document do not represent all the examples that may be implemented or that fall within the scope of the claims. The term "example" shall be interpreted to mean "serving as an example, instance, or illustration," and not "preferred" or "advantageous over other examples."

Articles such as "the," "a," and "an" can connote the singular or plural. The word "or" when used without a preceding "either" (or other similar language indicating that "or" is unequivocally meant to be exclusive, for example, only one of x or y) shall be interpreted to be inclusive (for example, "x or y" means one or both of x and y).

The term "and/or" shall also be interpreted to be inclusive (for example, "x and/or y" means one or both of x and y). In situations where "and/or" or "or" are used as a conjunction for a group of three or more items, then the group shall be interpreted to include one item alone, all the items together, or any combination or number of the items.

The terms "has," "contain(s)," and "include(s)" shall be interpreted to be synonymous with the term "comprise(s)" and as inclusive or open-ended such as to not exclude additional unrecited subject matter. Use of the four preceding terms also discloses and provides support for narrower alternative implementations, in which these terms are replaced by "consisting" or "consisting essentially of," which are closed as to exclude additional unrecited subject matter.

Unless otherwise indicated, all numbers or expressions, such as those expressing concentrations, ratios, counts, and the like, used in the specification (other than the claims) are understood to be modified in all instances by the term "approximately." At the very least, and not as an attempt to limit the application of the doctrine of equivalents to the claims, each numerical parameter recited in the specification or claims that is modified by the term "approximately" should be construed in light of the number of recited significant digits and by applying ordinary rounding techniques. All disclosed ranges are to be understood to encompass and provide support for claims that recite any subranges or any and all individual values subsumed by each range. For example, a stated range of "at least 90 percent" shall be construed as including support for at least 90 percent, at least 95 percent, at least 97 percent, at least 98 percent, at least 99 percent, at least 99.5 percent, at least 99.6 percent, at least 99.7 percent, at least 99.8 percent, and at least 99.9 percent.

The terms recited in the claims should be given their ordinary and customary meaning as determined by reference to relevant entries in widely used general dictionaries, relevant technical references, commonly understood meanings by those in the art, and the like with the understanding that the broadest meaning imparted by any one or combination of these sources should be given to the claim terms (for example, two or more relevant references should be combined to provide the broadest meaning of the combination of references) subject only to the following two exceptions: (a) when a term is used in a manner that is more expansive than its ordinary and customary meaning, then the term should be given its ordinary and customary meaning plus the additional expansive meaning, and (b) when a term has been explicitly defined to have a different meaning by reciting the term and its definition along with the phrase "in this disclosure" or similar language, then the term shall be limited to the definition (for example, this disclosure uses the word "chimeric" in reference to antibodies differently than as commonly used in the relevant arts, and the word "chimeric antibody" and similar words such as "chimeric IgG" shall be limited to the scope defined in this disclosure). References to specific examples shall not invoke the foregoing exception (b) or otherwise restrict the scope of the recited claim terms. Other than situations where the foregoing exception (b) applies, nothing contained in this document should be considered a disclaimer or disavowal of claim scope.

The subject matter recited in the claims is not coextensive with and should not be interpreted to be coextensive with any implementation, feature, or combination of features described or illustrated in this document. This is true even if only a single implementation of the feature or combination of features is illustrated and described.

The entire content of each document listed below is incorporated by reference into this document (the documents below are collectively referred to as the "incorporated documents"). If the same term is used in both this document and one or more of the incorporated documents, then the term should be interpreted to have the broadest meaning imparted by any one or combination of these sources unless the term has been explicitly defined to have a different meaning in this document. If there is an inconsistency between any incorporated document and this document, then this document shall govern. The incorporated subject matter should not be used to limit or narrow the scope of the explicitly recited or depicted subject matter.

U.S. Pat. No. 5,731,168 A, entitled "Method for making heteromultimeric polypeptides," granted Mar. 24, 1998;

U.S. Pat. No. 8,592,562 B2, entitled "Method for making antibody Fc-heterodimeric molecules using electrostatic steering effects," granted Nov. 26, 2013;

U.S. Pat. No. 9,505,848 B2, entitled "Engineered heterodimeric protein domains," granted Nov. 29, 2016;

U.S. Pat. No. 9,862,769 B2, entitled "Monoclonal antibodies against HER2," granted Jan. 9, 2018;

U.S. Pat. No. 10,011,858 B2, entitled "Methods for producing polypeptides by regulating polypeptide association," granted Jul. 3, 2018;

U.S. Pat. No. 10,344,050 B2, entitled "Production of heterodimeric proteins," granted Jul. 9, 2019;

U.S. Pat. No. 10,597,464 B2, entitled "Heterodimeric antibody Fc-containing proteins and methods for production thereof," granted Mar. 24, 2020;

Kabat, E. A. et al., "Sequences of proteins of immunological interest." 5th Edition-US Department of Health and Human Services, NIH publication No. 91-3242 (1991);

Shopes, B., "A genetically engineered human IgG mutant with enhanced cytolytic activity," THE JOURNAL OF IMMUNOLOGY, 1992 May 1; 148(9):2918-22;

Shopes, B., "A genetically engineered human IgG with limited flexibility fully initiates cytolysis via complement," MOLECULAR IMMUNOLOGY, 1993 April; 30(6):603-9; and van der Neut Kolfschoten, M. et al., "Anti-inflammatory activity of human IgG4 antibodies by dynamic Fab arm exchange," SCIENCE, 2007 Sep. 14; 317(5844): 1554-7.

What is claimed is:

1. A dimeric immunotherapeutic, comprising a first chimeric immunotherapeutic and a second chimeric immunotherapeutic, wherein:
the first chimeric immunotherapeutic comprises a first chimeric IgG that comprises a first light chain, a first heavy chain, a second light chain, and a second heavy chain, which each have an amino acid sequence numbered according to the EU numbering system;
the second chimeric immunotherapeutic comprises a second chimeric IgG that comprises a first light chain, a first heavy chain, a second light chain, and a second heavy chain, which each have an amino acid sequence numbered according to the EU numbering system;
the amino acid sequences of the first light chain of the first chimeric IgG and the first light chain of the second chimeric IgG are identical;
the amino acid sequences of the second light chain of the first chimeric IgG and the second light chain of the second chimeric IgG are identical;
the amino acid sequences of the first heavy chain of the first chimeric IgG and the first heavy chain of the second chimeric IgG are identical;
the amino acid sequences of the second heavy chain of the first chimeric IgG and the second heavy chain of the second chimeric IgG are identical;
the amino acid sequences of the first heavy chain of the first chimeric IgG and the first heavy chain of the second chimeric IgG each include a mutation of a native amino acid to a cysteine;
the cysteine of the amino acid sequence of the first heavy chain of the first chimeric IgG and the cysteine of the amino acid sequence of the first heavy chain of the second chimeric IgG form a disulfide bond with each other;
the amino acid sequences of the second heavy chain of the first chimeric IgG and the second heavy chain of the second chimeric IgG each lack the mutation;
the first chimeric immunotherapeutic is chimeric at least because the amino acid sequence of the first heavy chain of the first chimeric IgG comprises the mutation and the amino acid sequence of the second heavy chain of the first chimeric IgG lacks the mutation such that the first chimeric IgG comprises two different heavy chains;
the second chimeric immunotherapeutic is chimeric at least because the amino acid sequence of the first heavy chain of the second chimeric IgG comprises the mutation and the amino acid sequence of the second heavy chain of the second chimeric IgG lacks the mutation such that the second chimeric IgG comprises two different heavy chains;
the first chimeric IgG and the second chimeric IgG are both chimeric human IgG1s;
the native amino acid is S444;
the mutation is S444C;
the amino acid sequences of the first heavy chain of the first chimeric IgG and the first heavy chain of the second chimeric IgG each include a F405L mutation;
the amino acid sequences of the second heavy chain of the first chimeric IgG and the second heavy chain of the second chimeric IgG each include a K409R mutation;
the first heavy chain of the first chimeric IgG, the second heavy chain of the first chimeric IgG, the first heavy chain of the second chimeric IgG, and the second heavy chain of the second chimeric IgG each comprise a heavy chain variable region that has an identical amino acid sequence; and
the first light chain of the first chimeric IgG, the second light chain of the first chimeric IgG, the first light chain of the second chimeric IgG, and the second light chain of the second chimeric IgG each comprise a light chain variable region that has an identical amino acid sequence.

2. A dimeric immunotherapeutic, comprising a first chimeric immunotherapeutic and a second chimeric immunotherapeutic, wherein:
the first chimeric immunotherapeutic comprises a first chimeric IgG that comprises a first light chain, a first heavy chain, a second light chain, and a second heavy chain, which each have an amino acid sequence numbered according to the EU numbering system;

the second chimeric immunotherapeutic comprises a second chimeric IgG that comprises a first light chain, a first heavy chain, a second light chain, and a second heavy chain, which each have an amino acid sequence numbered according to the EU numbering system;

the amino acid sequences of the first light chain of the first chimeric IgG and the first light chain of the second chimeric IgG are identical;

the amino acid sequences of the second light chain of the first chimeric IgG and the second light chain of the second chimeric IgG are identical;

the amino acid sequences of the first heavy chain of the first chimeric IgG and the first heavy chain of the second chimeric IgG are identical;

the amino acid sequences of the second heavy chain of the first chimeric IgG and the second heavy chain of the second chimeric IgG are identical;

the amino acid sequences of the first heavy chain of the first chimeric IgG and the first heavy chain of the second chimeric IgG each include a mutation of a native amino acid to a cysteine;

the cysteine of the amino acid sequence of the first heavy chain of the first chimeric IgG and the cysteine of the amino acid sequence of the first heavy chain of the second chimeric IgG form a disulfide bond with each other;

the amino acid sequences of the second heavy chain of the first chimeric IgG and the second heavy chain of the second chimeric IgG each lack the mutation;

the first chimeric immunotherapeutic is chimeric at least because the amino acid sequence of the first heavy chain of the first chimeric IgG comprises the mutation and the amino acid sequence of the second heavy chain of the first chimeric IgG lacks the mutation such that the first chimeric IgG comprises two different heavy chains; and the second chimeric immunotherapeutic is chimeric at least because the amino acid sequence of the first heavy chain of the second chimeric IgG comprises the mutation and the amino acid sequence of the second heavy chain of the second chimeric IgG lacks the mutation such that the second chimeric IgG comprises two different heavy chains.

3. The dimeric immunotherapeutic of claim 2, wherein:
the first chimeric IgG and the second chimeric IgG are both chimeric human IgG1s;
the native amino acid is S444;
the mutation is S444C;
the amino acid sequences of the first heavy chain of the first chimeric IgG and the first heavy chain of the second chimeric IgG each include a F405L mutation;
the amino acid sequences of the second heavy chain of the first chimeric IgG and the second heavy chain of the second chimeric IgG each include a K409R mutation;
the first heavy chain of the first chimeric IgG, the second heavy chain of the first chimeric IgG, the first heavy chain of the second chimeric IgG, and the second heavy chain of the second chimeric IgG each comprise a heavy chain variable region that has an identical amino acid sequence; and
the first light chain of the first chimeric IgG, the second light chain of the first chimeric IgG, the first light chain of the second chimeric IgG, and the second light chain of the second chimeric IgG each comprise a light chain variable region that has an identical amino acid sequence.

4. The dimeric immunotherapeutic of claim 2, wherein:
the first heavy chain of the first chimeric IgG, the second heavy chain of the first chimeric IgG, the first heavy chain of the second chimeric IgG, and the second heavy chain of the second chimeric IgG each comprise a VH CDR1 region comprising an amino acid sequence that is identical to SEQ ID NO: 5;
the first heavy chain of the first chimeric IgG, the second heavy chain of the first chimeric IgG, the first heavy chain of the second chimeric IgG, and the second heavy chain of the second chimeric IgG each comprise a VH CDR2 region comprising an amino acid sequence that is identical to SEQ ID NO: 6;
the first heavy chain of the first chimeric IgG, the second heavy chain of the first chimeric IgG, the first heavy chain of the second chimeric IgG, and the second heavy chain of the second chimeric IgG each comprise a VH CDR3 region comprising an amino acid sequence that is identical to SEQ ID NO: 7;
the first light chain of the first chimeric IgG, the second light chain of the first chimeric IgG, the first light chain of the second chimeric IgG, and the second light chain of the second chimeric IgG each comprise a VL CDR1 region comprising an amino acid sequence that is identical to SEQ ID NO: 8;
the first light chain of the first chimeric IgG, the second light chain of the first chimeric IgG, the first light chain of the second chimeric IgG, and the second light chain of the second chimeric IgG each comprise a VL CDR2 region comprising an amino acid sequence that is identical to SEQ ID NO: 9; and
the first light chain of the first chimeric IgG, the second light chain of the first chimeric IgG, the first light chain of the second chimeric IgG, and the second light chain of the second chimeric IgG each comprise a VL CDR3 region comprising an amino acid sequence that is identical to SEQ ID NO: 10.

5. The dimeric immunotherapeutic of claim 2, wherein:
the amino acid sequence of the first light chain of the first chimeric IgG is identical to SEQ ID NO: 4;
the amino acid sequence of the first light chain of the second chimeric IgG is identical to SEQ ID NO: 4;
the amino acid sequence of the second light chain of the first chimeric IgG is identical to SEQ ID NO: 4;
the amino acid sequence of the second light chain of the second chimeric IgG is identical to SEQ ID NO: 4;
the amino acid sequence of the first heavy chain of the first chimeric IgG is identical to SEQ ID NO: 3;
the amino acid sequence of the first heavy chain of the second chimeric IgG is identical to SEQ ID NO: 3;
the amino acid sequence of the second heavy chain of the first chimeric IgG is identical to SEQ ID NO: 3; and
the amino acid sequence of the second heavy chain of the second chimeric IgG is identical to SEQ ID NO: 3.

6. The dimeric immunotherapeutic of claim 2, wherein:
the amino acid sequence of the first light chain of the first chimeric IgG comprises SEQ ID NO: 4;
the amino acid sequence of the first light chain of the second chimeric IgG comprises SEQ ID NO: 4;
the amino acid sequence of the second light chain of the first chimeric IgG comprises SEQ ID NO: 4;
the amino acid sequence of the second light chain of the second chimeric IgG comprises SEQ ID NO: 4;
the amino acid sequence of the first heavy chain of the first chimeric IgG comprises SEQ ID NO: 3;
the amino acid sequence of the first heavy chain of the second chimeric IgG comprises SEQ ID NO: 3;

the amino acid sequence of the second heavy chain of the first chimeric IgG comprises SEQ ID NO: 3; and the amino acid sequence of the second heavy chain of the second chimeric IgG comprises SEQ ID NO: 3.

7. The dimeric immunotherapeutic of claim 2, wherein:

the amino acid sequences of the first light chain of the first chimeric immunotherapeutic, the second light chain of the first chimeric immunotherapeutic, the first light chain of the second chimeric immunotherapeutic, and the second light chain of the second chimeric immunotherapeutic are identical; and the amino acid sequences of the first heavy chain of the first chimeric immunotherapeutic, the second heavy chain of the first chimeric immunotherapeutic, the first heavy chain of the second chimeric immunotherapeutic, and the second heavy chain of the second chimeric immunotherapeutic each have at least 90 percent sequence identity.

8. The dimeric immunotherapeutic of claim 2, wherein the amino acid sequences of the first light chain of the first chimeric immunotherapeutic, the second light chain of the first chimeric immunotherapeutic, the first light chain of the second chimeric immunotherapeutic, and the second light chain of the second chimeric immunotherapeutic are identical.

9. The dimeric immunotherapeutic of claim 2, wherein the amino acid sequences of the first heavy chain of the first chimeric immunotherapeutic, the second heavy chain of the first chimeric immunotherapeutic, the first heavy chain of the second chimeric immunotherapeutic, and the second heavy chain of the second chimeric immunotherapeutic each have at least 90 percent sequence identity.

10. The dimeric immunotherapeutic of claim 2, wherein:

the first heavy chain of the first chimeric IgG, the second heavy chain of the first chimeric IgG, the first heavy chain of the second chimeric IgG, and the second heavy chain of the second chimeric IgG each comprise a heavy chain variable region that has an identical amino acid sequence; and the first light chain of the first chimeric IgG, the second light chain of the first chimeric IgG, the first light chain of the second chimeric IgG, and the second light chain of the second chimeric IgG each comprise a light chain variable region that has an identical amino acid sequence.

11. The dimeric immunotherapeutic of claim 2, wherein:

the first chimeric IgG and the second chimeric IgG are both chimeric human IgG4s;

the amino acid sequences of the first heavy chain of the first chimeric IgG and the first heavy chain of the second chimeric IgG each include an arginine at amino acid position 409 and a leucine at amino acid position 405; and the amino acid sequences of the second heavy chain of the first chimeric IgG and the second heavy chain of the second chimeric IgG each include a lysine at amino acid position 409 and a phenylalanine at amino acid position 405.

12. The dimeric immunotherapeutic of claim 2, wherein:

the first chimeric IgG and the second chimeric IgG are both chimeric human IgG4s;

the amino acid sequences of the first heavy chain of the first chimeric IgG and the first heavy chain of the second chimeric IgG each include a lysine at amino acid position 409 and a phenylalanine at amino acid position 405; and the amino acid sequences of the second heavy chain of the first chimeric IgG and the second heavy chain of the second chimeric IgG each include an arginine at amino acid position 409 and a leucine at amino acid position 405.

13. The dimeric immunotherapeutic of claim 2, wherein:

the first chimeric IgG and the second chimeric IgG are both chimeric human IgG1s;

the native amino acid is S444;

the mutation is S444C;

the amino acid sequences of the first light chain of the first chimeric immunotherapeutic, the second light chain of the first chimeric immunotherapeutic, the first light chain of the second chimeric immunotherapeutic, and the second light chain of the second chimeric immunotherapeutic are identical; and the amino acid sequences of the first heavy chain of the first chimeric immunotherapeutic, the second heavy chain of the first chimeric immunotherapeutic, the first heavy chain of the second chimeric immunotherapeutic, and the second heavy chain of the second chimeric immunotherapeutic each have at least 90 percent sequence identity.

14. The dimeric immunotherapeutic of claim 2, wherein:

the first chimeric IgG and the second chimeric IgG are both chimeric human IgG1s;

the native amino acid is S444;

the mutation is S444C;

the amino acid sequences of the first heavy chain of the first chimeric IgG and the first heavy chain of the second chimeric IgG each include a F405L mutation; and the amino acid sequences of the second heavy chain of the first chimeric IgG and the second heavy chain of the second chimeric IgG each include a K409R mutation.

15. The dimeric immunotherapeutic of claim 2, wherein:

the first chimeric IgG and the second chimeric IgG are both chimeric human IgG1s;

the native amino acid is S444;

the mutation is S444C;

the amino acid sequences of the first heavy chain of the first chimeric IgG and the first heavy chain of the second chimeric IgG each include a K409R mutation; and the amino acid sequences of the second heavy chain of the first chimeric IgG and the second heavy chain of the second chimeric IgG each include a F405L mutation.

16. The dimeric immunotherapeutic of claim 2, wherein:

the first chimeric IgG and the second chimeric IgG are both chimeric human IgG1s;

the amino acid sequences of the first heavy chain of the first chimeric IgG and the first heavy chain of the second chimeric IgG each include a F405L mutation; and the amino acid sequences of the second heavy chain of the first chimeric IgG and the second heavy chain of the second chimeric IgG each include a K409R mutation.

17. The dimeric immunotherapeutic of claim 2, wherein:

the first chimeric IgG and the second chimeric IgG are both chimeric human IgG1s;

the amino acid sequences of the first heavy chain of the first chimeric IgG and the first heavy chain of the second chimeric IgG each include a K409R mutation; and the amino acid sequences of the second heavy chain of the first chimeric IgG and the second heavy chain of the second chimeric IgG each include a F405L mutation.

18. The dimeric immunotherapeutic of claim 2, wherein:
the first chimeric IgG and the second chimeric IgG are both chimeric human IgG1s;
the native amino acid is S444; and
the mutation is S444C.

19. The dimeric immunotherapeutic of claim 2, wherein:
the amino acid sequences of the first heavy chain of the first chimeric IgG and the first heavy chain of the second chimeric IgG each include an arginine at amino acid position 409 and a leucine at amino acid position 405; and
the amino acid sequences of the second heavy chain of the first chimeric IgG and the second heavy chain of the second chimeric IgG each include a lysine at amino acid position 409 and a phenylalanine at amino acid position 405.

20. The dimeric immunotherapeutic of claim 2, wherein:
the amino acid sequences of the first heavy chain of the first chimeric IgG and the first heavy chain of the second chimeric IgG each include a lysine at amino acid position 409 and a phenylalanine at amino acid position 405; and
the amino acid sequences of the second heavy chain of the first chimeric IgG and the second heavy chain of the second chimeric IgG each include an arginine at amino acid position 409 and a leucine at amino acid position 405.

* * * * *

```
                              SEQUENCE LISTING

Sequence total quantity: 10
SEQ ID NO: 1           moltype = DNA  length = 369
FEATURE                Location/Qualifiers
source                 1..369
                       mol_type = other DNA
                       organism = Synthetic construct
SEQUENCE: 1
caggtacagc tgcagcagtc aggggctgag gtgaagaagc ctgggtcctc ggtgaaggtc  60
tcctgcaagg cttctggagg caccttcagc agctatgcta tcagctgggt gcgacaggcc 120
cctggacaag ggcttgagtg gatgggaagg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gagaccctcc 300
gaagaggtgg tagctgctta cggtgctttt gatatctggg gccaagggac cacggtcacc 360
gtctcaagc                                                         369

SEQ ID NO: 2           moltype = DNA  length = 336
FEATURE                Location/Qualifiers
source                 1..336
                       mol_type = other DNA
                       organism = Synthetic construct
SEQUENCE: 2
gaaattgtgc tgactcagtc tccactctcc ctgcccgtca gacctgggga gccggcctcc  60
atctcctgca gggctagtca gagcctcctg cgtagtgacg gattcaacta cttggattgg 120
tacctgcaga agccagggca gtctccacag ctcctggtct atttgggttc taatcgggcc 180
tccggggtcc ctgacaggtt cagtggcagt ggatcaggca cagatttac actgaaaatc 240
agcagagtgg aggctgagga tgttggggtt tattactgca tgcaagctgt acaaactccg 300
tacttttttg gccaggggac caagctggag atcaaa                           336

SEQ ID NO: 3           moltype = AA   length = 123
FEATURE                Location/Qualifiers
source                 1..123
                       mol_type = protein
                       organism = Synthetic construct
SEQUENCE: 3
QVQLQQSGAE VKKPGSSVKV SCKASGGTFS SYAISWVRQA PGQGLEWMGR IIPILGIANY  60
AQKFQGRVTI TADKSTSTAY MELSSLRSED TAVYYCARPS EEVVAAYGAF DIWGQGTTVT 120
VSS                                                               123

SEQ ID NO: 4           moltype = AA   length = 112
FEATURE                Location/Qualifiers
source                 1..112
                       mol_type = protein
                       organism = Synthetic construct
SEQUENCE: 4
EIVLTQSPLS LPVRPGEPAS ISCRASQSLL RSDGFNYLDW YLQKPGQSPQ LLVYLGSNRA  60
SGVPDRFSGS GSGTDFTLKI SRVEAEDVGV YYCMQAVQTP YIFGQGTKLE IK         112

SEQ ID NO: 5           moltype = AA   length = 10
FEATURE                Location/Qualifiers
source                 1..10
                       mol_type = protein
                       organism = Synthetic construct
SEQUENCE: 5
GGTFSSYAIS                                                         10

SEQ ID NO: 6           moltype = AA   length = 17
FEATURE                Location/Qualifiers
source                 1..17
                       mol_type = protein
                       organism = Synthetic construct
SEQUENCE: 6
RIIPILGIAN YAQKFQG                                                 17

SEQ ID NO: 7           moltype = AA   length = 16
FEATURE                Location/Qualifiers
source                 1..16
                       mol_type = protein
                       organism = Synthetic construct
```

```
SEQUENCE: 7
ARPSEEVVAA YGAFDI                                                                   16

SEQ ID NO: 8           moltype = AA  length = 16
FEATURE                Location/Qualifiers
source                 1..16
                       mol_type = protein
                       organism = Synthetic construct
SEQUENCE: 8
RASQSLLRSD GFNYLD                                                                   16

SEQ ID NO: 9           moltype = AA  length = 7
FEATURE                Location/Qualifiers
source                 1..7
                       mol_type = protein
                       organism = Synthetic construct
SEQUENCE: 9
LGSNRAS                                                                              7

SEQ ID NO: 10          moltype = AA  length = 10
FEATURE                Location/Qualifiers
source                 1..10
                       mol_type = protein
                       organism = Synthetic construct
SEQUENCE: 10
MQAVQTPYIF                                                                          10
```